United States Patent
Cates et al.

(10) Patent No.: US 6,818,008 B1
(45) Date of Patent: *Nov. 16, 2004

(54) PERCUTANEOUS PUNCTURE SEALING METHOD

(75) Inventors: Christopher U. Cates, Atlanta, GA (US); Robert C. Hornak, Smyrna, GA (US); Frank H. Stephens, Jr., Dunwoody, GA (US)

(73) Assignee: CCH Associates, Inc., Atlanta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,017

(22) Filed: Sep. 12, 1997

Related U.S. Application Data

(63) Continuation of application No. 08/247,069, filed on May 20, 1994, now abandoned, which is a continuation-in-part of application No. 07/817,587, filed on Jan. 7, 1992, now Pat. No. 6,056,768.

(51) Int. Cl.⁷ .............................................. A61B 19/00
(52) U.S. Cl. ....................................................... 606/213
(58) Field of Search .................................. 606/213, 214

(56) References Cited

U.S. PATENT DOCUMENTS

| | | | |
|---|---|---|---|
| 1,432,482 A | 10/1922 | Merriam | |
| 1,563,881 A | 1/1925 | Vetter | |
| 2,647,294 A | 8/1953 | Davis .......................... 24/223 |
| 3,223,083 A | * 12/1965 | Cobey .................... 606/214 X |
| 4,645,488 A | 2/1987 | Matukas ...................... 604/59 |
| 4,645,491 A | 2/1987 | Evans ........................ 604/117 |
| 4,660,560 A | 4/1987 | Klein .................... 604/101.05 |
| 4,744,364 A | 5/1988 | Kensey .................... 128/334 R |
| 4,790,819 A | 12/1988 | Li et al. ........................ 604/59 |
| 4,852,568 A | 8/1989 | Kensey ........................ 128/325 |
| 4,871,094 A | 10/1989 | Gall et al. ................... 222/386 |
| 4,874,368 A | 10/1989 | Miller et al. .................. 604/82 |
| 4,890,612 A | * 1/1990 | Kensey ........................ 606/213 |
| 4,909,251 A | 3/1990 | Seelich ........................ 606/213 |
| 4,929,246 A | 5/1990 | Sinofsky ......................... 606/8 |
| 5,021,059 A | 6/1991 | Kensey ........................ 606/213 |
| 5,053,046 A | 10/1991 | Janese .................... 606/213 X |
| 5,061,274 A | 10/1991 | Kensey ........................ 606/213 |
| 5,108,421 A | * 4/1992 | Fowler .................... 604/15 X |
| 5,129,882 A | 7/1992 | Weldon et al. ........... 606/213 X |
| 5,141,515 A | 8/1992 | Eberbach ..................... 606/213 |
| 5,147,316 A | 9/1992 | Castillenti ................... 604/164 |
| 5,192,300 A | 3/1993 | Fowler ........................ 606/213 |
| 5,239,982 A | 8/1993 | Trauthen ..................... 604/117 |
| 5,290,310 A | * 3/1994 | Makower et al. ........... 606/213 |
| 5,320,639 A | * 6/1994 | Rudnick ..................... 606/213 |
| 5,370,660 A | * 12/1994 | Weinstein et al. ....... 606/213 X |
| 5,383,899 A | * 1/1995 | Hammerslag ............... 606/214 |
| 5,391,183 A | * 2/1995 | Janzen et al. ............... 606/213 |
| 5,419,765 A | * 5/1995 | Weldon et al. .......... 606/213 X |

FOREIGN PATENT DOCUMENTS

| | | | | |
|---|---|---|---|---|
| AU | 652808 | * | 9/1992 | .................. 606/214 |
| AU | B-12498/95 | | 9/1992 | ........... A61L/25/00 |

OTHER PUBLICATIONS

"Fibrijet™ Surgical Sealant Delivery Systems," published by Micromedics, Inc., publication date unknown.

* cited by examiner

*Primary Examiner*—Michael H. Thaler
(74) *Attorney, Agent, or Firm*—Jason A. Bernstein; Powell, Goldstein, Frazer & Murphy LLP

(57) ABSTRACT

A method of sealing percutaneous punctures in a patient's body that open into an internal body cavity using a sealing material such as a fibrin adhesive while preventing the sealing material from entering the body cavity. The apparatus for delivering the sealing material is also disclosed.

6 Claims, 22 Drawing Sheets

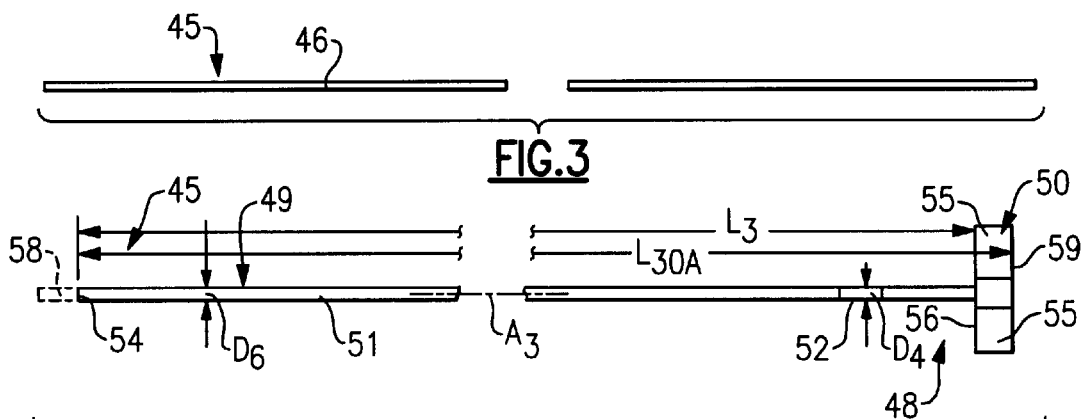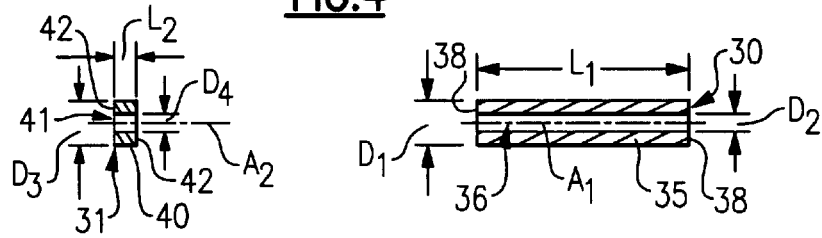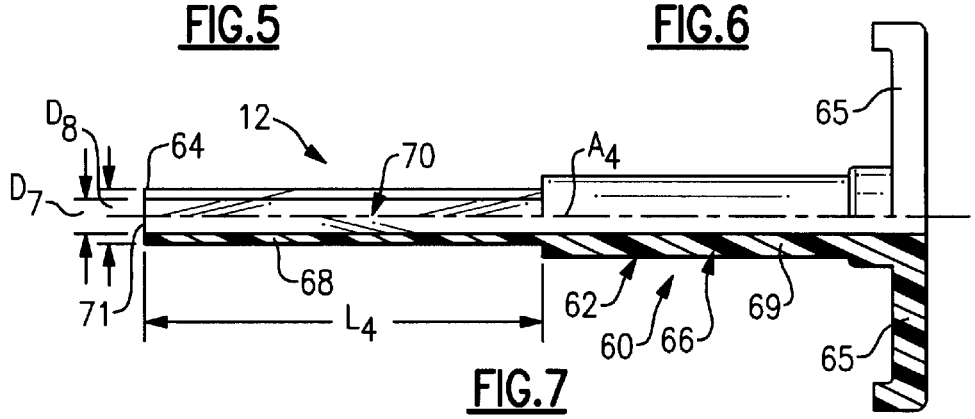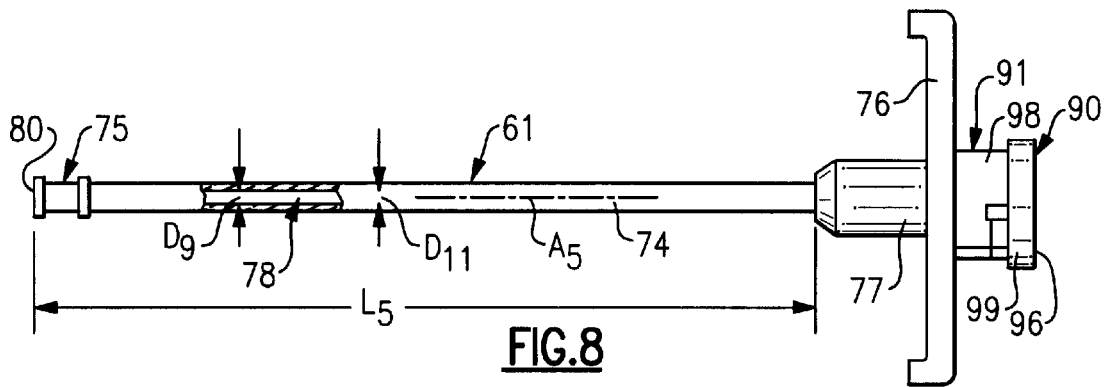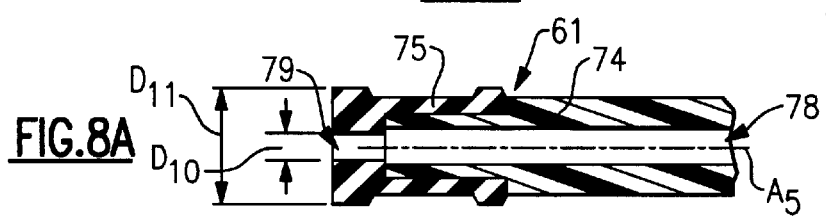

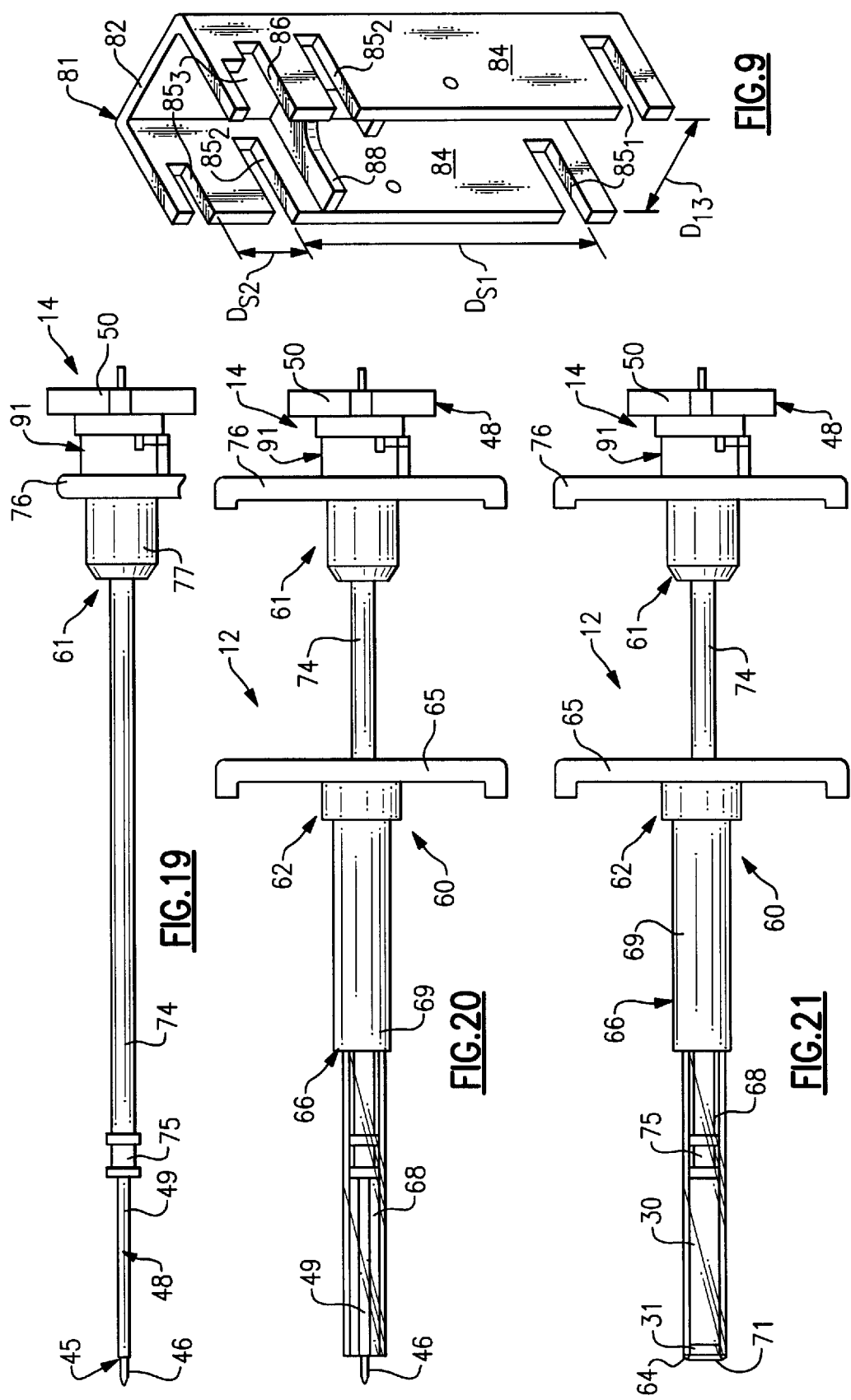

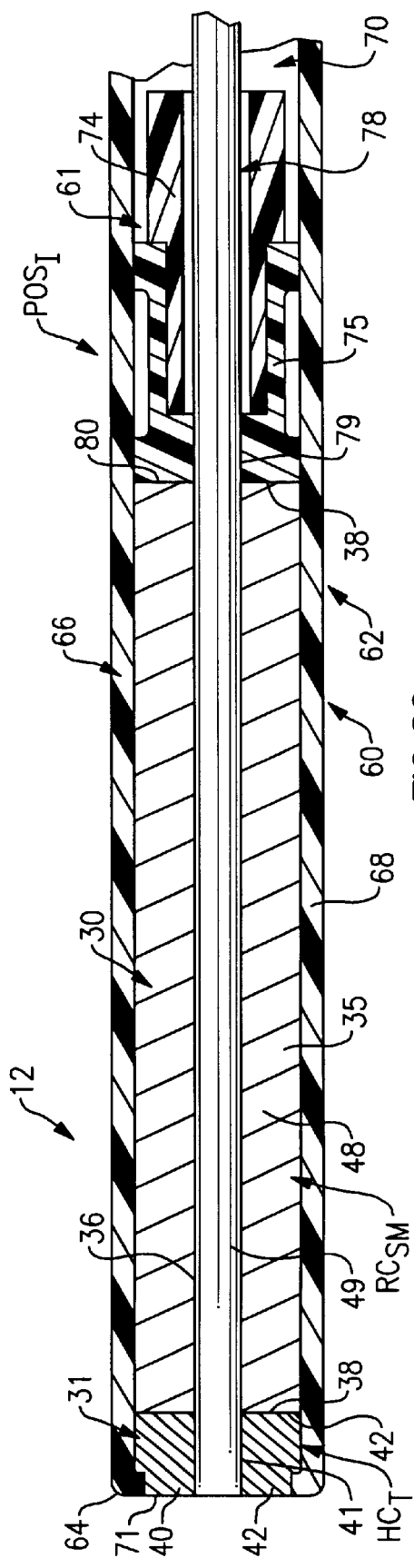
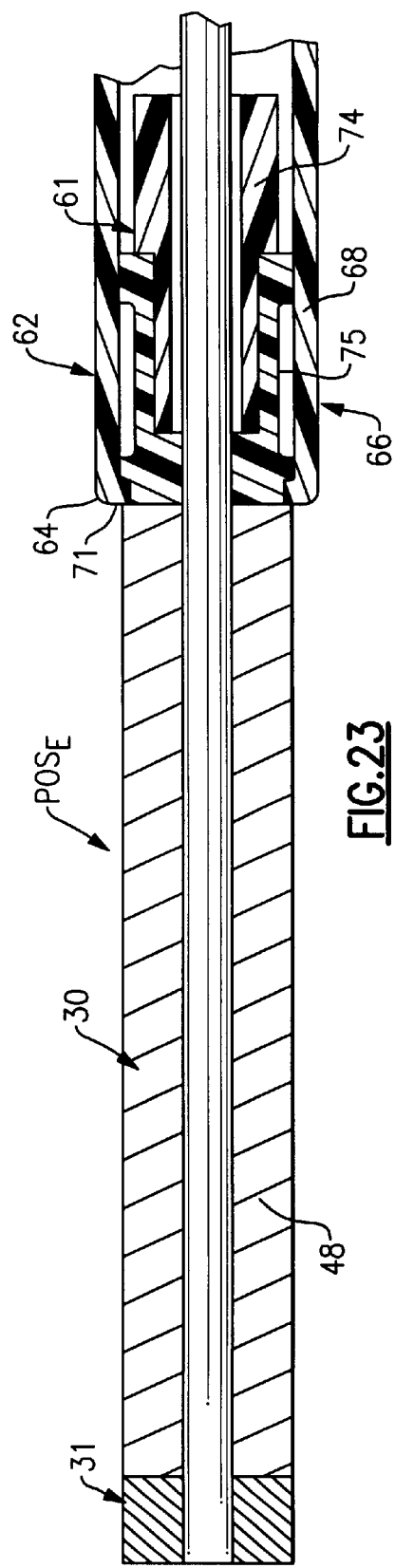
FIG. 22
FIG. 23

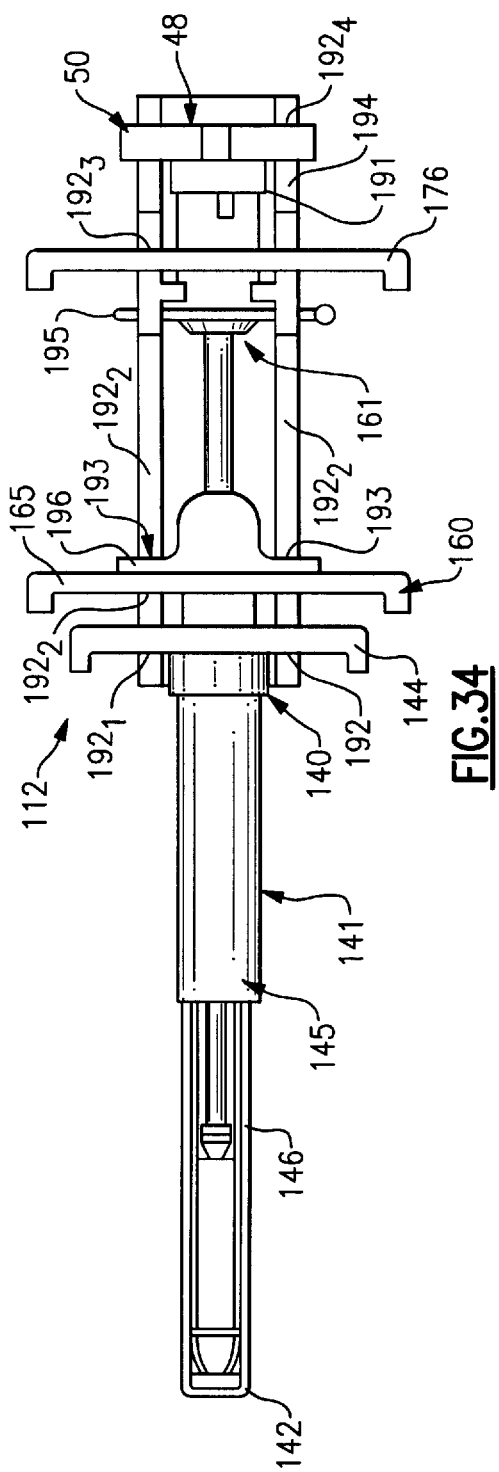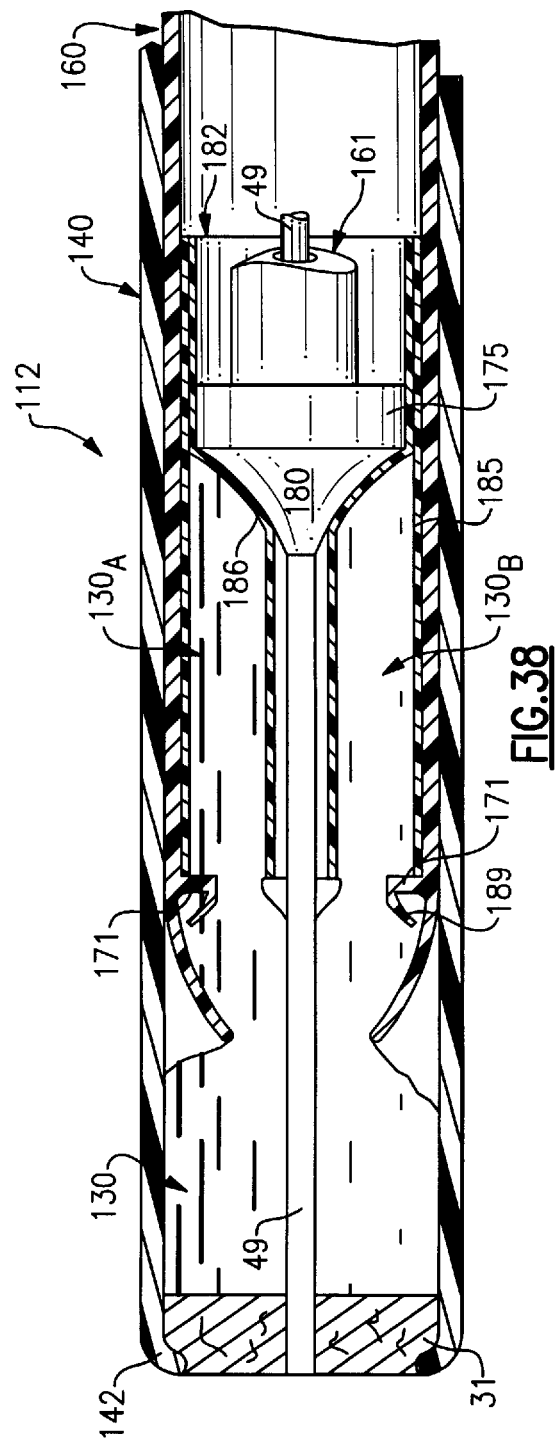

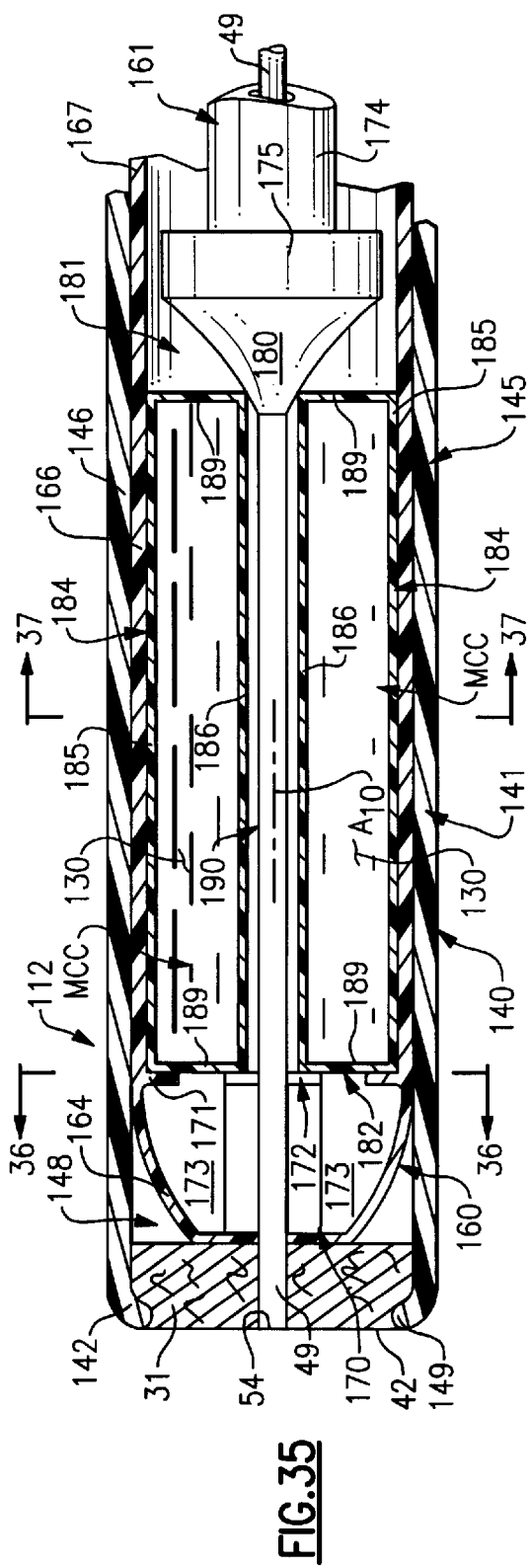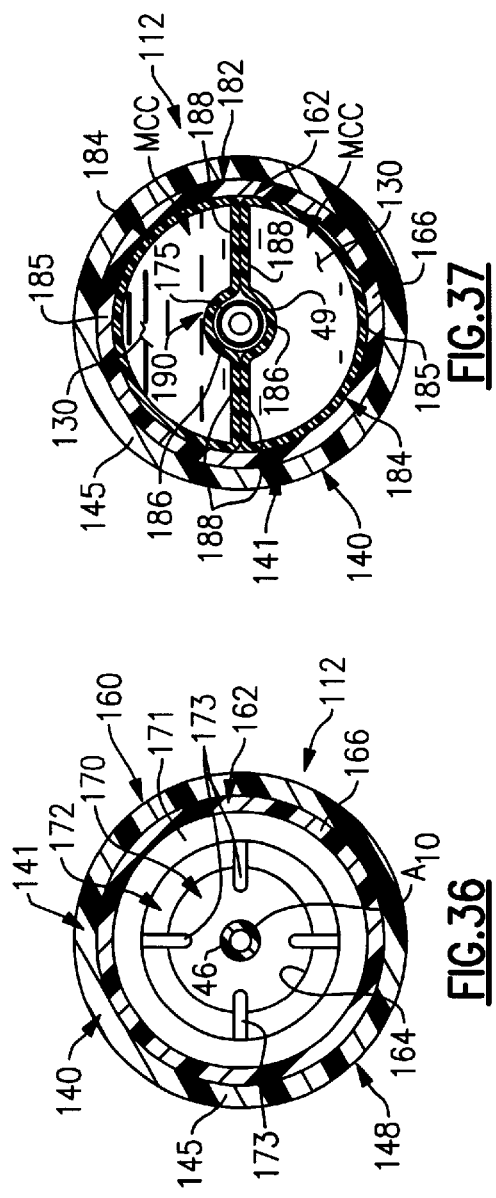

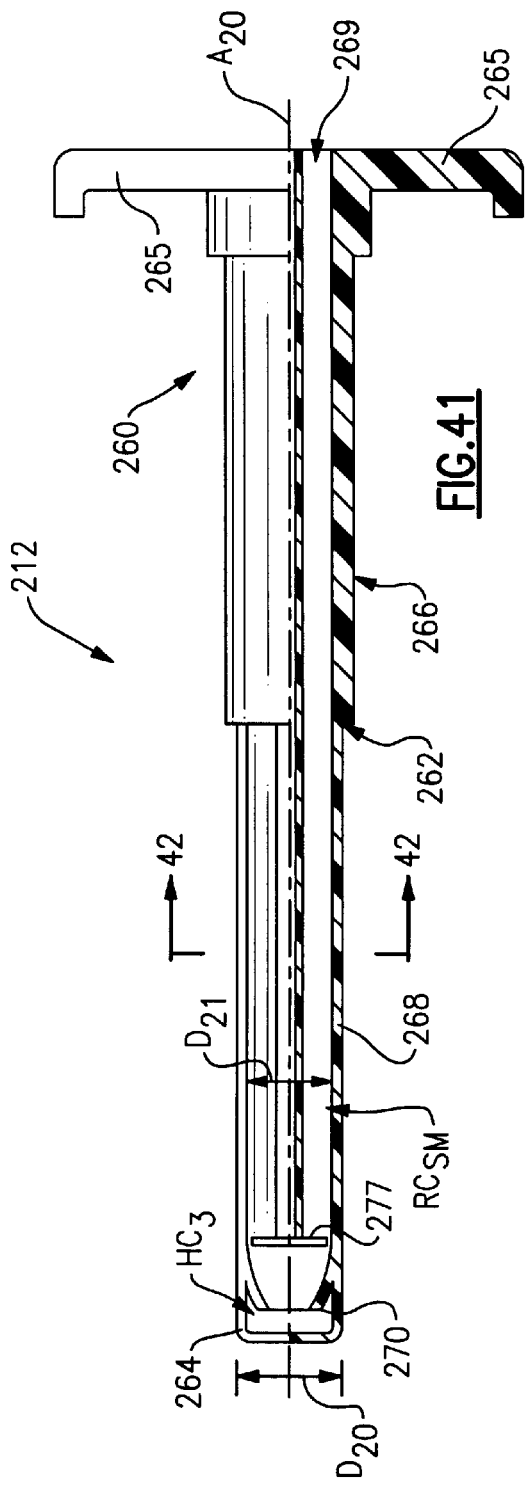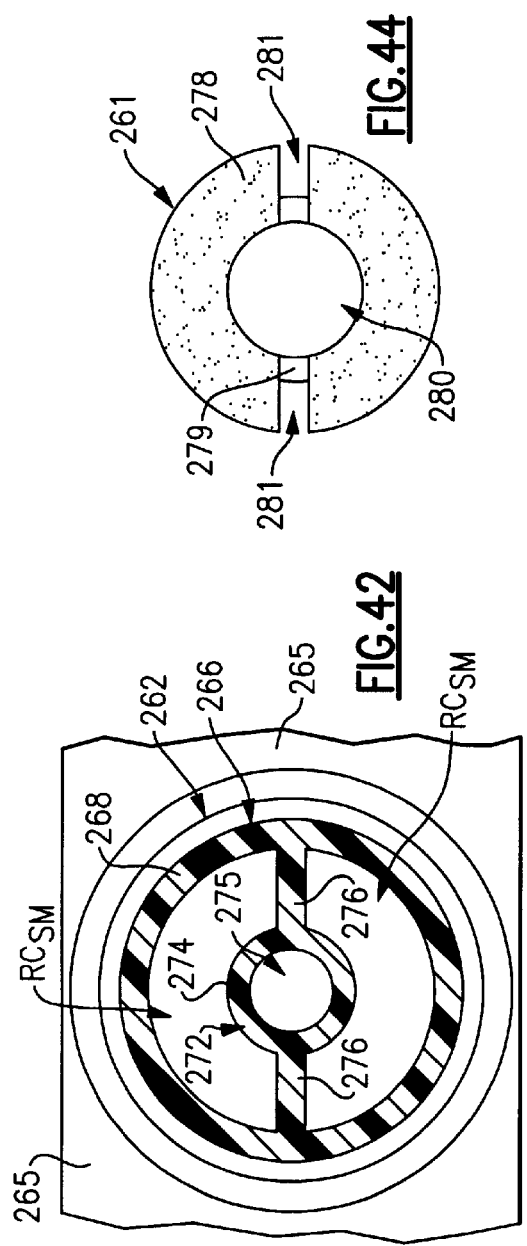
FIG. 41
FIG. 42
FIG. 44

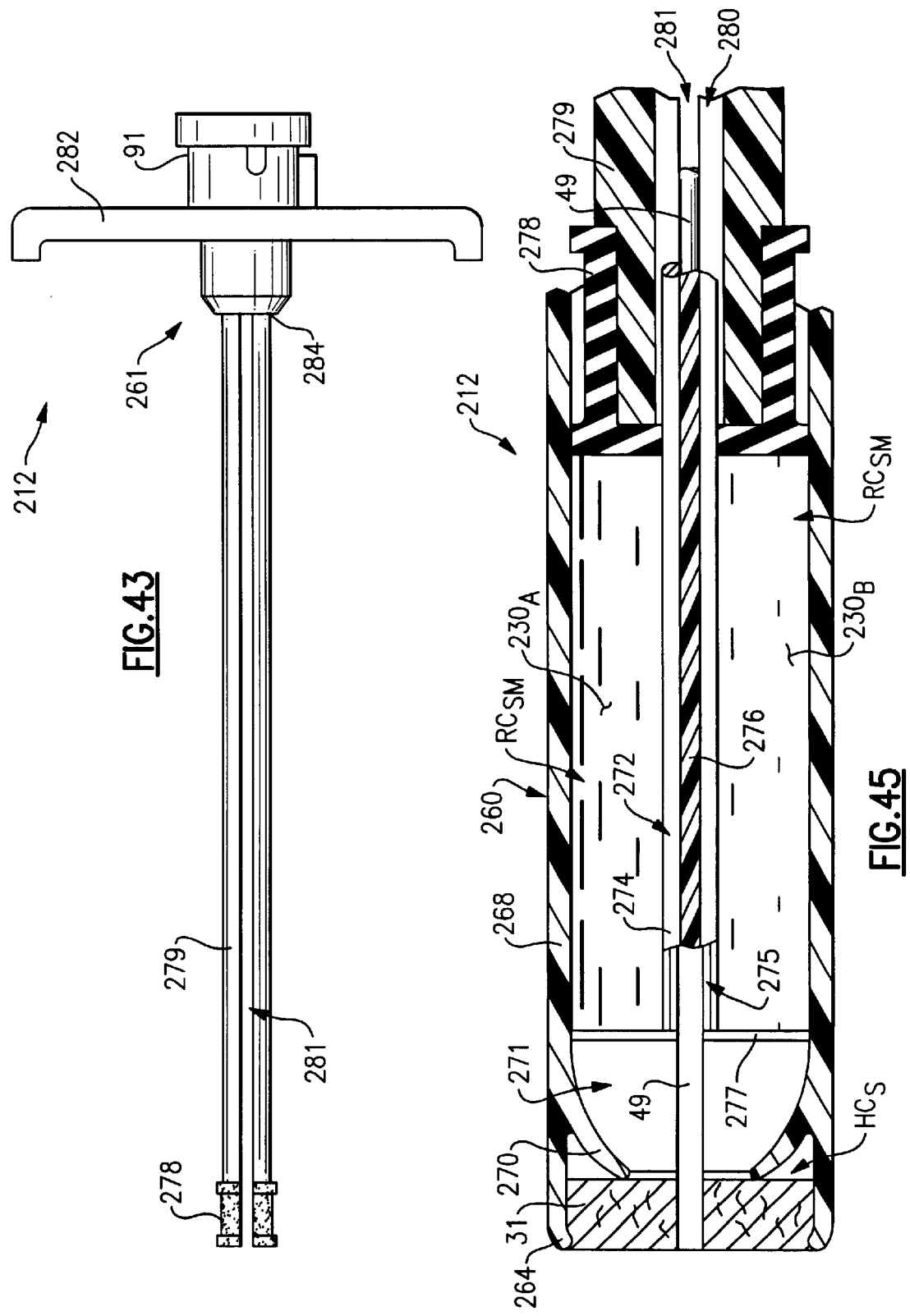

PERCUTANEOUS PUNCTURE SEALING METHOD

CROSS-REFERENCE TO RELATED APPLICATIONS

The present application is a continuation of application Ser. No. 08/247,069, filed May 20, 1994, now abandoned, which is a continuation-in-part of Ser. No. 07/817,587, filed Jan. 7, 1992, now U.S. Pat. No. 6,056,768, the disclosures of both of which are incorporated herein.

BACKGROUND OF THE INVENTION

This invention relates generally to the sealing of surgically produced punctures for different medical procedures and more particularly to the sealing of such punctures using a sealing material ejected into the puncture.

Certain medical procedures require the percutaneous puncturing of the body tissue of a patient to gain access to a cavity in the body to perform the medical procedure. One general example of such procedures is the puncturing the body tissues and the blood vessel wall to gain access to the interior of the vascular system of the patient for the procedure to be conducted. Such procedures that commonly require the percutaneous puncturing of the blood vessel wall are balloon angioplasty procedures, arteriography, venography, angiography and other diagnostic procedures that use blood vessel catheterization. Examples of other procedures using this technique are laparoscopic surgery and other microscopic surgery techniques using a small incision through one or more sections of body tissue to gain access to the body cavity in which the surgical procedure is to take place. In each of these techniques, it is necessary to reclose the incisions or punctures through the body tissue after the surgical procedure. Examples of such prior art techniques are set forth in the following patents:

| U.S. Pat. No. | Inventor | Issue Date | Class/Subclass |
|---|---|---|---|
| 4,890,612 | Kensey | 1/1990 | 623/1X |
| 5,021,059 | Kensey et al. | 6/1991 | 606/213 |
| 5,053,046 | Janese | 10/1991 | 606/213X |
| 5,108,421 | Fowler | 4/1992 | 606/213 |
| 5,129,882 | Welborn et al. | 7/1992 | 606/213X |
| 5,141,515 | Eberbach | 8/1992 | 606/213 |
| 5,147,316 | Castillenti | 9/1992 | 604/174X |
| 5,290,310 | Makower et al. | 3/1994 | 606/213 |

One of the primary problems associated with the prior art is the inability to insure that the puncture or incision is sealed along its length while at the same time insuring that part of the sealing material does not protrude from the puncture into the body cavity after the puncture has been sealed. This is particularly critical when sealing punctures into blood vessels because any dislodgement of the sealing material from the puncture can cause an embolus while any protruding sealing material from the puncture into the blood vessel can serve to undesirably restrict the blood flow past the site (i.e. thrombosis).

SUMMARY OF THE INVENTION

These and other problems and disadvantages associated with the prior art are overcome by the invention disclosed herein by providing a technique for sealing a percutaneous puncture or opening through the body tissue into a body cavity such as a blood vessel while insuring that the sealing material will be contained within the puncture. The sealing material may be a preformed member or a flowable material which sets up after it is injected into the puncture. The seal may be formed by a blood clot within the puncture or by a sealing material such as a fibrin adhesive which positively bonds the body tissue around the puncture together to seal it.

The method of the invention comprises depositing a biocompatible sealing material such as a biocompatible adhesive along at least that portion of the puncture adjacent the body cavity in a patient while preventing passage of the adhesive out of the end of the puncture into the body cavity, and allowing the adhesive to bond the body tissue around the puncture to close the puncture without passage of the adhesive into the body cavity. The sealing material may be prevented from passing out of the end of the puncture into the body cavity by temporarily closing that end of the puncture through the body of the patient opening into the body cavity while the sealing material is deposited into the puncture. The temporary closing mechanism may be removed through the sealing material after the seal is established. The sealing material may be a single or multiple component fibrin adhesive. To maintain the adhesive in a prepared but uncured condition, it may be maintained in a frozen state or it may be mixed as an incident to the depositing of the adhesive into the puncture. Likewise, where the fibrin is activated by exposure to some condition such as irradiation with ultraviolet light, exposure to heat, or the like, it may be so exposed to such condition just prior to or during installation in the puncture. To insure access through the sealing material to the end of the puncture at the body cavity for the temporary closing mechanism, a central tube may be preinstalled through the sealing material through which the temporary sealing mechanism passes as the sealing material is installed in the puncture. The central tube also allows the collapsed expandable portion of the temporary sealing mechanism to be withdrawn therethrough after the sealing material is installed. A bioabsorbable separator member may also be installed between the leading end of the sealing material and the temporarily closed end of the puncture to insure that none of the sealing material inadvertently passes out of the end of the puncture and into the body cavity. The separator member may also promote sealing of the puncture in addition to the sealing material. The method of the invention is also directed to preparing a fibrin adhesive for use in bonding body tissue comprising the steps of forming the fibrin adhesive into a prescribed shape, and then freezing the fibrin adhesive while in the prescribed shape to maintain the shape. The method may also include mounting the frozen fibrin adhesive on a central tube extending therethrough. Where the central tube is flexible, it may be internally supported while the frozen fibrin is installed thereon.

The apparatus of the invention is directed to an installation system for delivering a sealing material along the length of a percutaneous puncture that opens into a cavity in the body of a patient comprising a delivery assembly sized to be inserted into the puncture and defining a material carrying chamber therein with a discharge opening therefrom through which the sealing material can be discharged. A plunger means is slidably received in the chamber in the delivery assembly for selectively forcing the sealing material in the chamber out of the discharge opening as the plunger means and said delivery assembly are moved relative to each other so that the plunger means can be located at an initial position in the chamber in the delivery assembly with the sealing material in the chamber between the plunger means and the discharge opening while the delivery assembly is inserted into the puncture until the projecting end of the delivery assembly is located in the vicinity of that end of the puncture opening into the body cavity. The delivery assembly may further comprise a sheath member sized to fit in the puncture and defining the assembly projecting leading end thereon and a passage therein opening onto the projecting leading end, and a delivery member sized to fit in the passage in the sheath member and defining the material receiving chamber therein, a projecting discharge end thereon, and an ejection opening from the material carrying chamber through the projecting discharge end from which the sealing material can be discharged. The delivery member can be slidably inserted into the sheath member leading end first to a first position in which the ejection opening is located in the vicinity of the projecting leading end of the sheath member and so that the sealing material can be ejected into the passage in the sheath member as the delivery member is withdrawn along the sheath member while the sheath member is maintained substantially axially fixed in the puncture. The projecting leading end of the delivery assembly may define a temporary holding chamber therein opening onto the projecting end which is sized to receive the preformed separator member therein so that the preformed separator member is substantially flush with the projecting end of the delivery assembly whereby the preformed separator member will be located in the puncture between the sealing material and that end of the puncture opening into the body cavity of the patient. Retaining means may be provided on the delivery assembly for engaging the separator member to retain said separator member in the temporary holding chamber until the delivery assembly is being withdrawn from the puncture. The material carrying chamber has alternative designs to accommodate the sealing material in either a preformed substantially solid form or a flowable form. In the flowable form, the material carrying chamber may be divided into subcompartments if the sealing material is a multiple component material. Likewise, the material carrying chamber may be adapted to receive a cartridge of the sealing material in flowable form so that the plunger forces the sealing material out of the cartridge. Where the sealing material is a multiple component liquid, the delivery assembly may be equipped with a mixing chamber for mixing the components as an incident to the ejection of the components into the puncture. Also, where the sealing material is activated by radiation such as ultraviolet light, at least a section of the delivery assembly may be made transmissive to the radiation to expose the sealing material to such radiation either just before, during, or after the installation of the sealing material in the puncture.

The apparatus of the invention may also include locating means for selectively fixing the position of the plunger means relative to that end of the puncture opening into the body cavity as the delivery assembly is retracted along the plunger means to cause the sealing material to be discharged into the puncture as the delivery assembly is withdrawn from the puncture. The locating means may also serve to center the delivery assembly as it is being installed. The locating means may also serve to temporarily seal that end of the puncture opening into the body cavity and may include an expandable closing means having a first transverse configuration smaller than the transverse cross-sectional configuration of the puncture to pass through the puncture to the vicinity of the body cavity and a second transverse cross-sectional configuration larger than the transverse cross-sectional configuration of the puncture for closing the puncture, remote actuation means for selectively changing the closing means from the first transverse cross-sectional configuration to the second cross-sectional configuration while in the body cavity to selectively close the puncture at that end opening into the body cavity, and interconnect means connecting the closing means and the remote actuation means and passing out of the patient's body through the puncture to be manually engaged. The delivery assembly and the plunger means define alignable central passages therethrough sized for the interconnect means to pass therethrough. The locating means may further comprise locking means for connecting the plunger means to the interconnect means and include a base member defining a base passage therethrough sized to slidably receive the interconnect means therethrough and fixedly connected to the plunger means, and a locking member defining a locking passage therethrough sized to slidably receive the interconnect means therethrough with the said locking member movably mounted on the base member so that the locking passage can be moved from a release position in which the locking passage is in axial alignment with the base passage so that the locking member can be positioned in a locking position in which the locking passage is out of axial alignment with the base passage so that the interconnect means will be gripped between the base and locking members to fixedly hold the interconnect member relative to the base and locking members and thus the plunger means.

These and other features and advantages of the invention will become more clearly understood upon consideration of the following detailed description and accompanying drawings wherein like characters of reference designate corresponding parts throughout the several views and in which:

BRIEF DESCRIPTION OF THE DRAWINGS

FIG. 3 is a side view of the support mandrel of the internal guide arrangement of the invention;

FIG. 4 is a side view of the central guide and positioning tube of the internal guide arrangement of the invention;

FIG. 5 is a longitudinal cross-sectional view of the separator member of the invention;

FIG. 6 is a longitudinal cross-sectional view of the preformed sealing material member of the invention;

FIG. 7 is a side view shown in half section of the delivery assembly of a first embodiment on the installation arrangement of the invention;

FIG. 8 is a side view of the plunger means of the first embodiment on the installation arrangement of the invention;

FIG. 8A is an enlarged longitudinal cross-sectional view of the projecting end of the plunger means seen in FIG. 8;

FIG. 9 is an enlarged perspective view of the discharge preventing means of the invention;

FIG. 19 is a side view showing an alternate method of loading the sealing material in the delivery assembly with the preformed sealing material and the separator member mounted on the central guide tube;

FIG. 20 is a side view showing the sealing preassembly installed in the delivery assembly;

FIG. 21 is a side view showing the plunger means installed the delivery assembly with the sealing preassembly;

FIG. 22 is an enlarged longitudinal cross-sectional view of the projecting end of the assembly as seen in FIG. 18 or 21 with the parts in the initial position;

FIG. 23 is a view like FIG. 22 with the parts in the ejected position;

FIG. 34 is a side view of the second embodiment of the installation arrangement assembled;

FIG. 35 is an enlarged longitudinal cross-sectional view of a portion of the second embodiment of the assembled installation arrangement;

FIG. 36 is a cross-sectional view taken along line 36—36 in FIG. 35;

FIG. 37 is a cross-sectional view taken along line 37—37 in FIG. 35;

FIG. 38 is a view similar to FIG. 35 showing the sealing material being dispensed into the sheath member;

FIG. 41 is an enlarged side view of the delivery assembly of a third embodiment of the installation arrangement of the invention shown in half section;

FIG. 42 is a transverse cross-sectional view taken generally along line 42—42 in FIG. 41;

FIG. 43 is side view of the plunger means of the third embodiment of the invention;

FIG. 44 is an enlarged projecting end view of the plunger means of the third embodiment of the invention;

FIG. 45 is a longitudinal cross-sectional view of the assembled third embodiment of the installation arrangement.

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

The invention disclosed herein can be used to close or seal percutaneous punctures made through the body tissue of a patient to gain access to a body cavity of a patient. Access through these percutaneous punctures allows the physician to carry out various procedures in the body cavity for examination, surgery, treatment and the like. While not meant to be limiting, the invention is illustrated being used to seal the percutaneous punctures made to gain access to blood vessels in patients for various procedures. It will be appreciated that the invention is applicable to the sealing of any percutaneous puncture to a body cavity.

Figure 24:
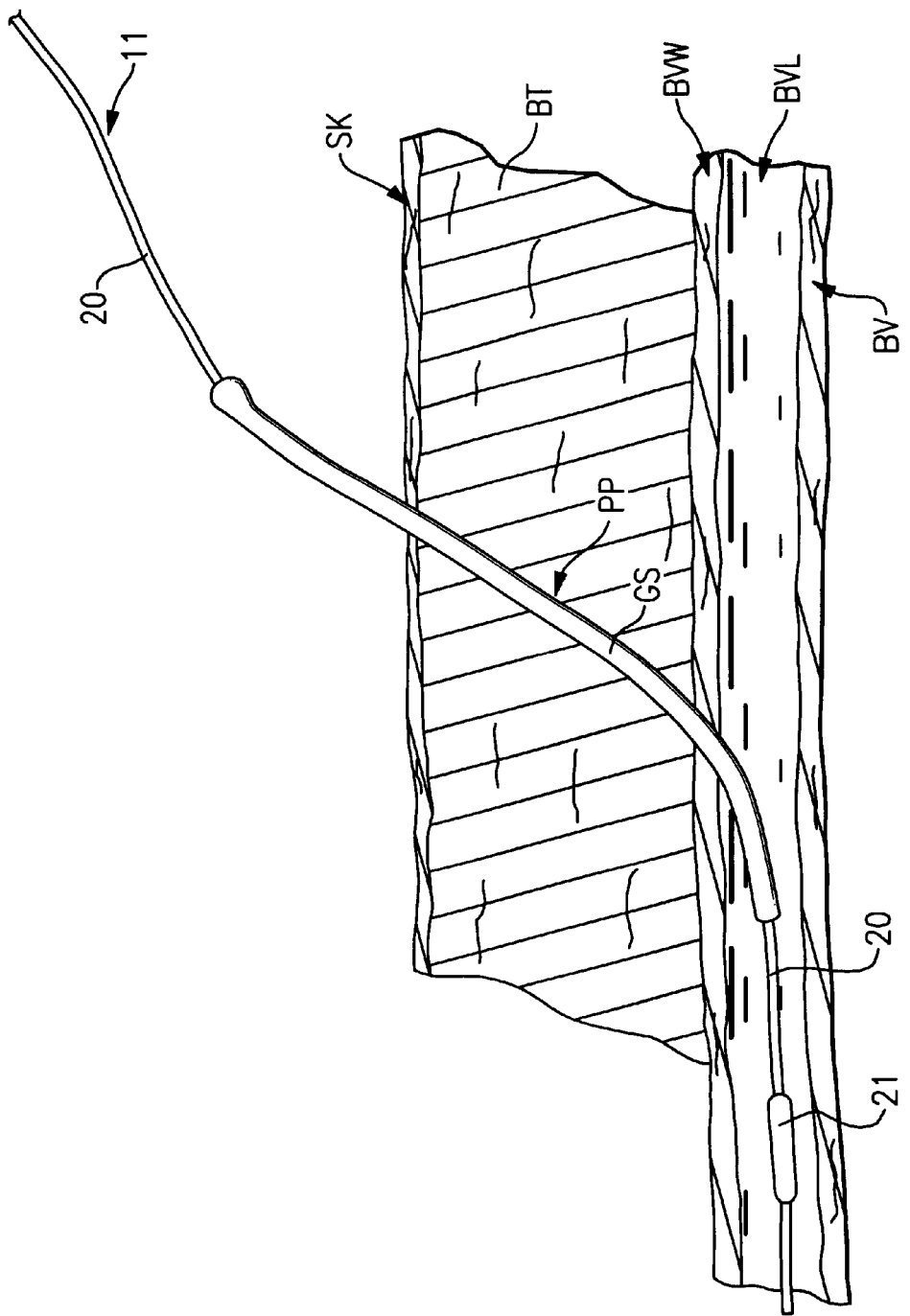
FIGS. 24–30 illustrate the installation of the embodiment of the invention seen in FIGS. 3–23.

The sealing system 10 of the invention is illustrated being used to seal a percutaneous puncture PP seen in FIG. 24 made through the skin SK, body tissue BT and the wall BVW of a blood vessel BV as an incident to a medical procedure. Typically, the blood vessel BV used is a femoral artery in the groin region with a relatively large vessel passage or lumen BVL to facilitate locating the blood vessel and permits a sufficiently large puncture to be made through the wall BVW thereof to carry out the procedure. Medical procedures which are typically performed through such a puncture are angioplasty and other procedures which pass a catheter or other type probe into and along the blood vessel lumen BVL. When such a procedure is performed, an initial percutaneous puncture with an appropriate needle is made from the patient's skin through the tissue and the blood vessel wall into the blood vessel lumen and a guide wire installed. The needle is then removed leaving the guide wire in place and a tapered introducer guide sheath GS is installed over the guide wire to enlarge the puncture so as to permit easier access to the blood vessel. The guide sheath GS serves to keep the passage open and prevent further damage to the tissue and skin around the passage during the medical procedure. This sheath GS assists in the installation of the sealing system 10 as will become more apparent.

Figure 1:
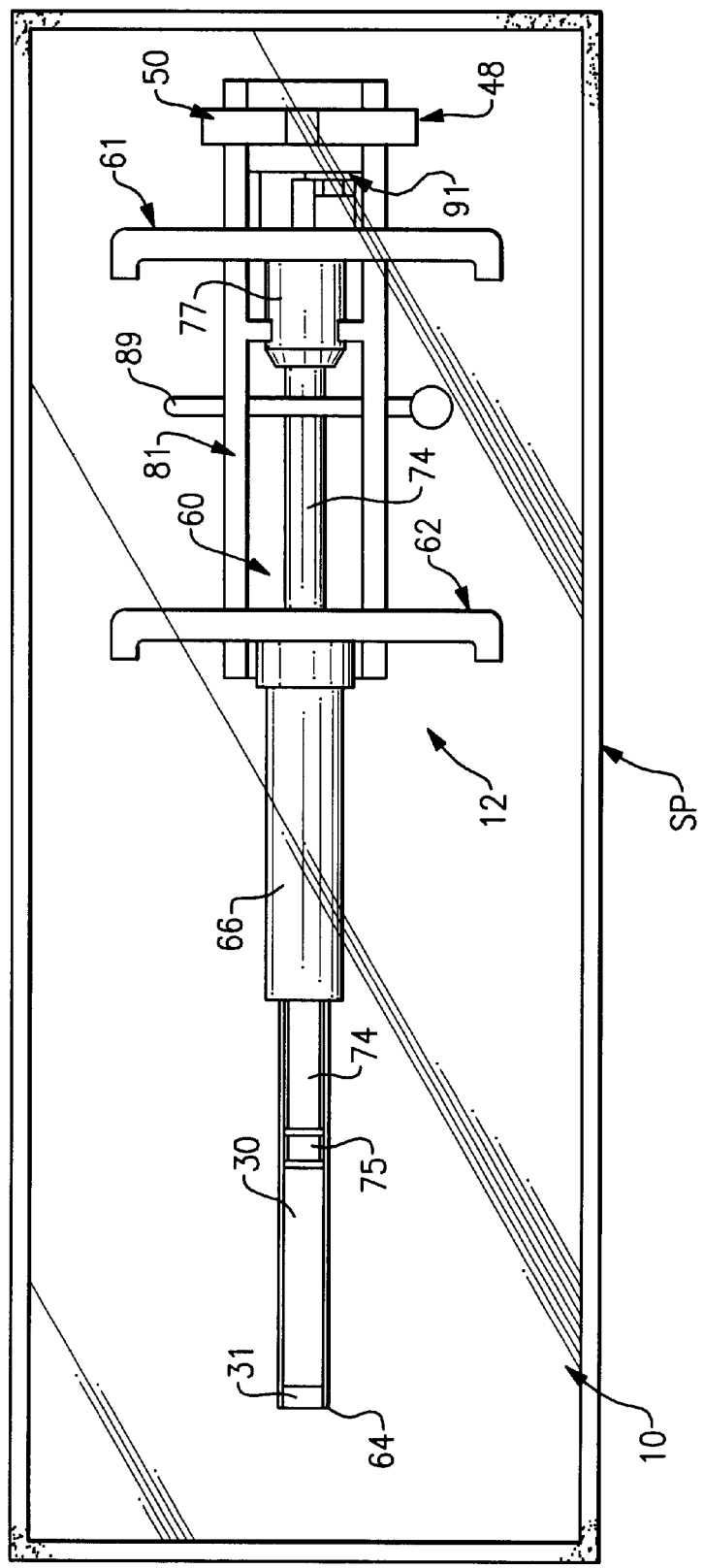
FIG. 1 is a side view of the installation arrangement of the invention.
Figure 2:
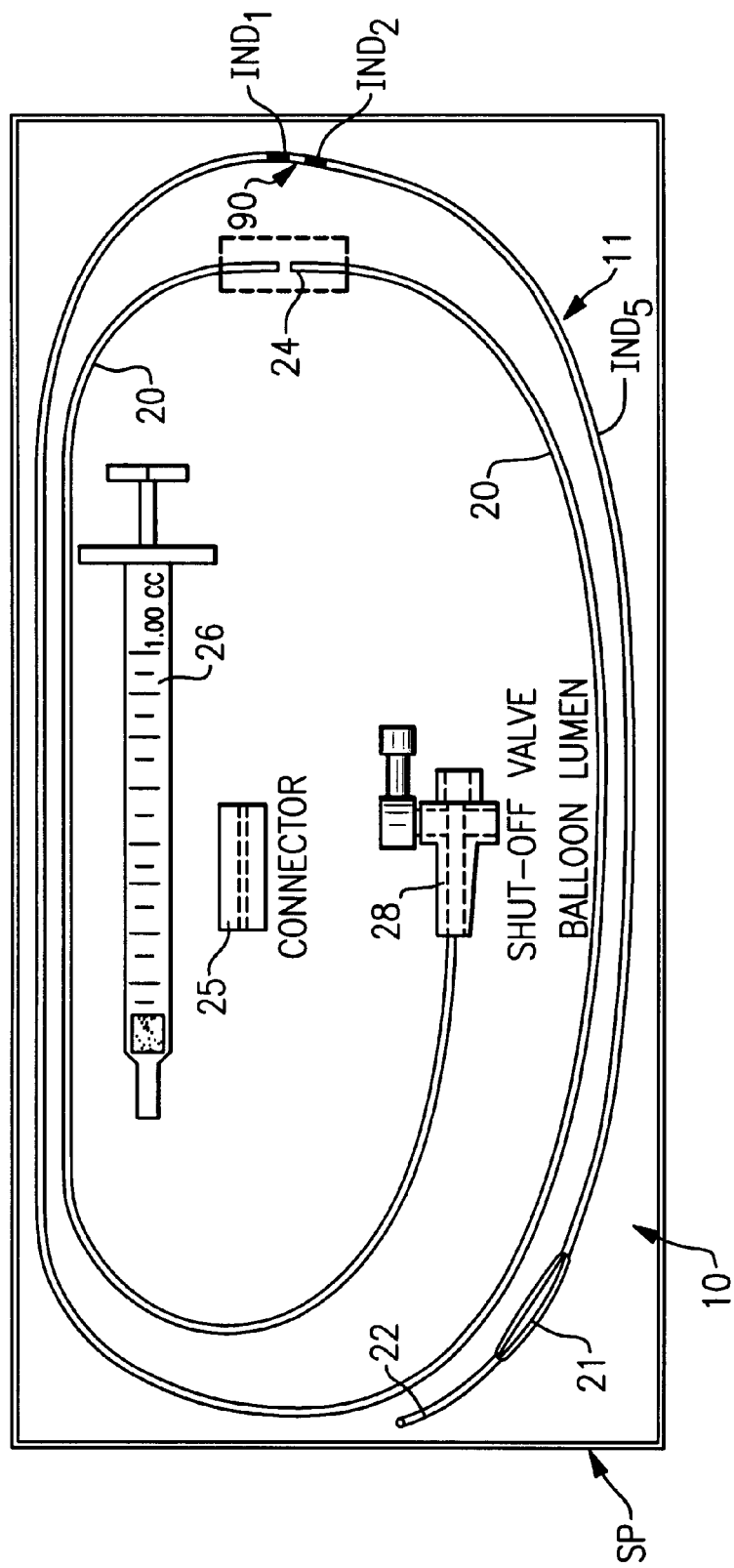
FIG. 2 is a side view of the temporary locating and sealing arrangement of the invention.
Figure 25:
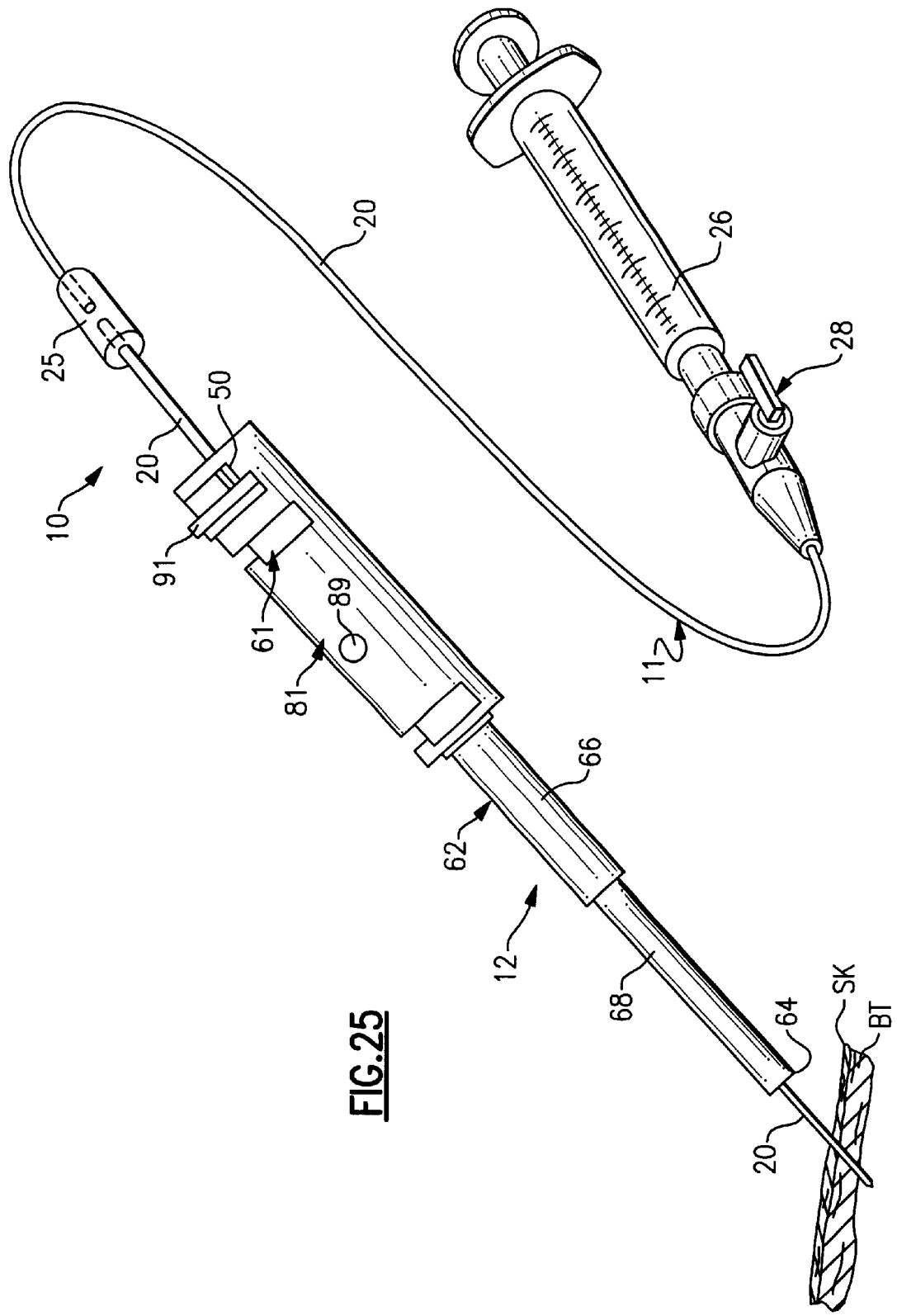
Figure 26:
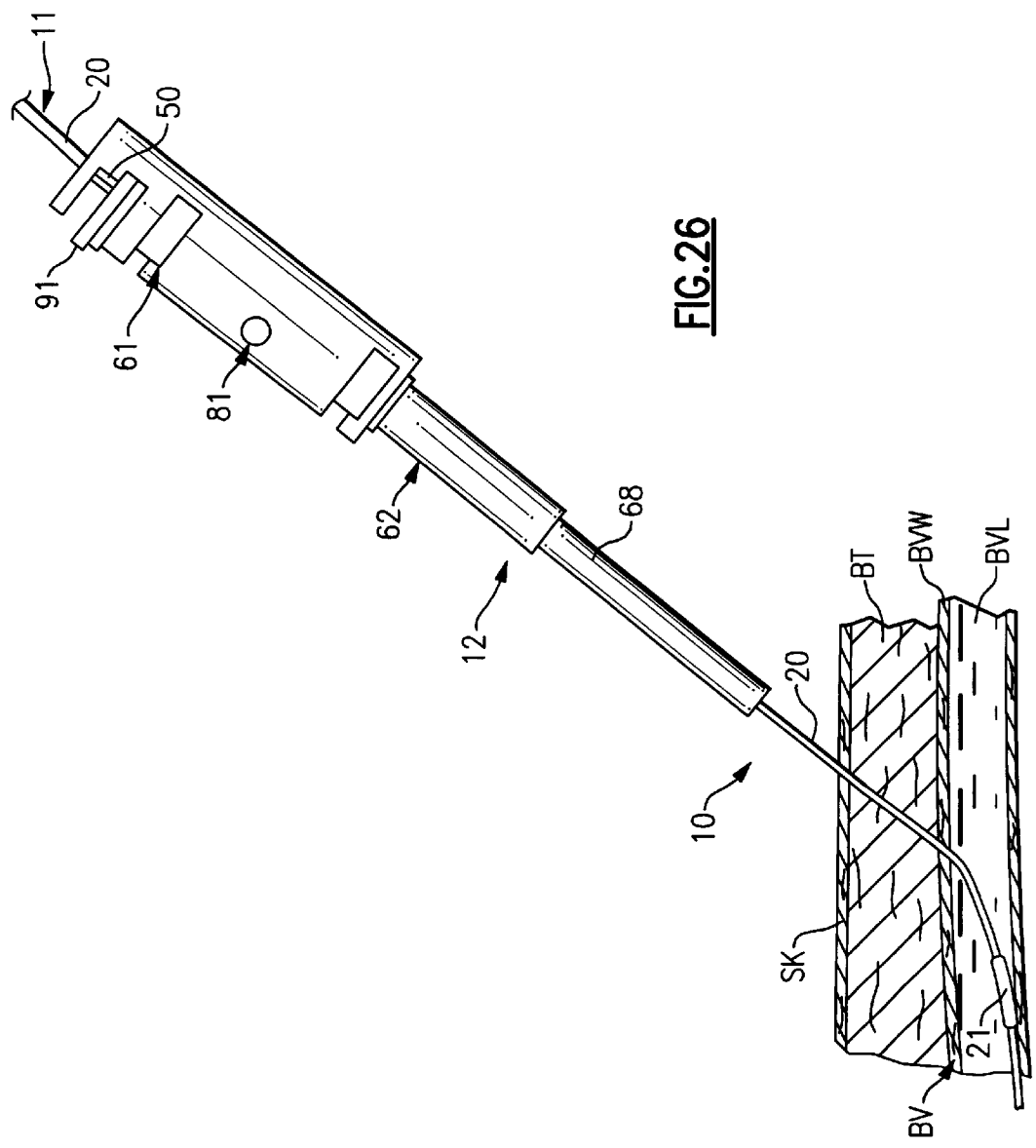

Referring to FIGS. 1 and 2, it will be seen that the sealing system 10 embodying the invention includes generally a temporary sealing arrangement 11, an installation arrangement 12, and an interconnect means 14 that permits the position of the installation arrangement 12 relative to the temporary sealing arrangement to be accurately controlled. The sealing arrangement 11 and installation arrangement 12 are illustrated stored in separate sterile packaging SP of well known construction. The temporary sealing arrangement 11 is inserted into the blood vessel lumen BVL through the introducer guide sheath GS as seen in FIG. 24 and then the sheath removed leaving the temporary sealing arrangement 11 in place as seen in FIGS. 25 and 26. The temporary sealing arrangement 11 serves to temporarily seal the interior end of the puncture PP opening into the blood vessel lumen BVL while the sealing material for sealing the puncture PP is placed with the installation arrangement. After the sealing material is installed, the temporary sealing arrangement 11 and the installation arrangement 12 are removed.

The sealing material used in the sealing of the puncture may be any of a number of different biocompatible materials as long as the material has the capability of maintaining the puncture sealed long enough for it to heal or form a sealing coagulum. The sealing material may be a material that actually bonds the body tissue at the puncture together such as a biocompatible adhesive or it may be a material that promotes the formation of a coagulum such as collagen. The sealing material may be installed in a preformed form or may be flowable when installed. The biocompatible adhesive may contain fibrin to promote bonding and may be a single or multiple component. As will become more apparent, multiple component sealing material may be mixed as an incident to the installation of the sealing material. Some sealing material can be activated by some condition to which the material is exposed such as a specified temperature or radiation exposure. For instance, some fibrin adhesives are activated by exposure to ultraviolet radiation. The invention contemplates the use of any of these sealing materials. For sake of brevity, the invention is disclosed being used to install a fibrin adhesive in a preformed state and in a flowable state. A collagen member is also illustrated being used in combination with the fibrin adhesive to serve as a separator member between the fibrin and the end of the puncture.

Temporary Sealing Arrangement:

The temporary sealing arrangement 11 illustrated in FIG. 2 is used with all embodiments of the installation arrangement 12. The temporary sealing arrangement 11 includes an elongate flexible control member 20 on the leading end of which is mounted an expandable tamponading member 21. The control member 20 is designed for the projecting end 22 thereof to pass through the guide sheath GS into the blood vessel lumen BVL. The control member 20 is separated intermediate its length with the tamponading member 21 on the leading portion thereof. The length of this leading portion of the control member 20 is sufficient to project out through the puncture exteriorly of the patient and allow the installation arrangement to fit thereover. The projecting end 22 may extend through the tamponading member 21 sufficiently for the control member 20 to still extend into the blood vessel lumen BVL after the tamponading member is removed from the patient so that the tamponading member 21 can be reinserted if necessary in the event of a failure. The exterior end 24 of the leading portion of member 20 connects with a coupling 25 for connection to an expanding mechanism 26 through the trailing section of the control member 20 for selectively expanding the tamponading member 21 from a collapsed condition as seen by solid lines in FIG. 2 closely adhering to the control member outside surface to an expanded condition as will become more apparent.

It will be appreciated that the tamponading member 21 may be mechanically, electrically, pneumatically or hydraulically expanded and collapsed without departing from the scope of the invention. The particular expanded exterior configuration of the tamponading member 21 can be selected depending on the particular circumstances of use. The criteria that is used to determine the particular size and configuration is the blood vessel condition at the puncture PP and the cross-sectional size and shape of the blood vessel lumen BVL in the vicinity of the puncture PP. The largest cross-sectional dimension of the expanded tamponading member 21 must be small enough for the member 21 to be pulled back against the interior end of the puncture PP without dragging or hanging up in the blood vessel lumen BVL. It has been found that an expanded dimension in one direction for the member 21 that is at least about 1.5 times larger than the puncture PP is satisfactory to prevent the tamponading member 21 from being pulled back through the puncture PP under typical conditions. That portion of the tamponading member 21 at the puncture PP must be larger than the size of the puncture PP to insure sealing when the tamponading member 21 is pulled back up against the interior end of the puncture PP as will become more apparent. While different expanded sizes may be used, dimensions on the order of 0.150–0.200 inch (3.8–5.1 mm) should be successful under typical conditions where the puncture PP is made with a 4 french needle.

Without limiting the scope of the invention, the particular temporary sealing assembly 11 illustrated is a balloon catheter with the tamponading member 21 illustrated in FIG. 2 as a small inflatable balloon which can be inflated to a size and configuration sufficiently larger than the blood vessel wall puncture PP to prevent the expanded balloon member 21 from being pulled back through the puncture PP while at the same time not hanging up in the blood vessel lumen BVL in its expanded condition. In the expanded condition, the member 21 has a puncture facing surface formed at the radius between the balloon 21 and control member 20 that serves to substantially center the control member 20 in the end of the puncture PP and maintain the end of the puncture PP closed. This is because the balloon 21 will shift in the end of the puncture until the force exerted on the balloon by the blood vessel wall and the body tissue is equally distributed around the control member 20. The inflatable balloon member 21 may be made out of any suitable material such as latex. The balloon member 21 is inflated and deflated through the control member 20 as will become more apparent.

The control member 20 is a thin elongate flexible member considerably smaller than the puncture PP. Typically, the diameter of the control member 20 is about 0.03 inch. The leading portion of the control member 20 is sufficiently long to extend from within the blood vessel lumen BVL out through the puncture PP exteriorly of the patient so that it can be manually manipulated and is also long enough for the guide sheath GS to be removed thereover and the delivery arrangement 12 to be passed thereon while the tamponading member 21 remains in the blood vessel lumen BVL. To permit the balloon member 21 to be inflated, the control member 20 defines an inflation lumen therethrough that extends from and communicates with the interior of the balloon member 21 along the length of the member 20 through the coupling 25. Thus, the balloon tamponading member 21 can be inflated and deflated through the lumen from a position external of the patient.

The balloon member 21 is inflated by any convenient fluid inflation device such as the syringe 26 illustrated. Typically, the syringe 26 or other inflation device will be of the same type as that already used in balloon angioplasty and is connected to the exterior end of the control member 20 through a valve 28 used to selectively seal the balloon lumen. The inflation fluid under pressure from the syringe 26 flows along the inflation lumen in the control member 20 into the balloon member 21 to selectively inflate same. The syringe 26 is also used to recollapse the balloon member 21 when it is to be withdrawn as will become more apparent.

Sealing Material Preassembly:

The first embodiment of the installation arrangement 12 is used to install the sealing material in a preformed state. While any preformed sealing material member may be installed, the member 30 illustrated is a fibrin adhesive that can be maintained in an uncured condition by freezing. Along with the member 30, a separator member 31 is also provided to separate the member 30 from the blood vessel lumen BVL as will become more apparent. While different materials may be used for the separator member 31, it is illustrated as being made out of collagen.

As seen in FIG. 6, the preformed member 30 is tubular with an outside diameter $D_1$, selected to fit in that portion of the installation arrangement 12 that fits in the puncture PP as will become more apparent. The tubular side wall 35 of the member 30 defines a central passage 36 therethrough with diameter $D_2$ for use in mounting the member 30 on the installation arrangement 12 and is larger than the outside diameter of the control member 20 of the temporary sealing arrangement as will become more apparent. The opposed ends 38 of the side wall 35 are arranged normal to the central axis A, thereof. The length $L_1$, of the member 30 is selected to correspond generally to the length of the puncture likely to be encountered. While the dimensions may be varied to meet the particular application, one expected set of dimensions is a length $L_1$ of about 1 inch, an outside diameter $D_1$ of about 0.110 inch, and a passage diameter $D_2$ of about 0.035 inch. It is anticipated that the member 30 will be made by pouring the sealing material that is normally at least semi-liquid at room temperature either into the installation arrangement 12 itself or into a separate preformed mold and then freezing the sealing material while maintained in the installation arrangement or separate mold. When the sealing material is frozen in the installation arrangement, it is ready for use. After the member 30 is frozen in the separate mold, it is appropriately removed from the mold while still frozen.

The separator member 31 seen in FIG. 5 has an annular disk shaped side wall 40 with a central axis $A_2$ and an outside diameter $D_3$ substantially the same as that of the sealing material member 30. The separator side wall 40 defines a central passage 41 therethrough along axis $A_2$ with a diameter $D_4$ about the same as or slightly smaller than the diameter $D_2$ of the passage 36 through the sealing material member 30. The opposed end surfaces 42 on the side wall 40 are oriented normal to the central axis $A_2$. The length $L_2$ of the member 31 is selected so that the member 31 is as thin as practical but still has sufficient strength to maintain the separation between the sealing material in member 30 and the end of the puncture PP. While not meant to be limiting, one length range that is satisfactory is about 0.125–0.250 inch.

Internal Guide Arrangement

An internal guide arrangement 45 is provided for use in internally supporting the members 30 and 31 in the installation assembly 12. The internal guide arrangement 45 may include a support mandrel 46 seen in FIG. 3 and a central guide tube assembly 48 best seen in FIG. 4.

The central guide tube assembly 48 serves to protect the interior of the members 30 and 31 during installation as the collapsed tamponading member 21 and control member 20 on the temporary sealing arrangement 11 are moved through the members 30 and 31. Guide tube assembly 48 includes an elongate guide tube 49 with a positioning handle 50 on one end thereof. The guide tube 49 is an extruded member with a very thin tubular side wall 51 about its central axis $A_3$. The side wall 51 defines a central passage 52 therethrough which is sized to slidably receive the collapsed balloon member 21 and control member 20 of the temporary sealing arrangement 11 therethrough. In the particular example illustrated, the outside diameter $D_5$ of the tube 49 is about 0.035 inch while the inside diameter $D_6$ is about 0.033 inch.

The positioning handle 50 is mounted on that end of the guide tube 49 opposite its projecting end 54 and facilitates manual positioning of the guide tube. The handle 50 also serves as a stop to limit projection of tube 50 into the installation arrangement 12. The handle 50 has a pair of opposed radially projection wings 55 to be manually grasped to remove the guide tube assembly 48 from within the installation arrangement 12 and the members 30 and 31 once installation is complete. The forward edge 56 on the handle 50 is oriented normal to axis $A_3$ to abut the trailing end of the installation arrangement 12 during the installation of the members 30 and 31 as will become more apparent.

The tube 49 has a length greater than that of the installation arrangement 12 so that, when the forward edge 56 of the handle 50 abuts the trailing end of installation arrangement, the projecting end 54 of the guide tube 49 is flush with the leading end of the installation arrangement. The finished length $L_3$ is selected to correspond to the overall length of the installation arrangement in its initial position as seen in FIG. 1 while the overall finished length $L_{30A}$ of the tube assembly 48 is used as a locating means for locating the sealing member 30 and the separator member 31 in the puncture PP as will be further explained.

The tube 49 may be made out of any material that does not adversely react with the sealing material member 30, the separator member 31, or the body tissue of the patient. One material which is satisfactory is polypropylene. While not required, it has been found that having the tube 49 flexible is advantageous to assist in its installation and removal. The tube 49 is designed to fit inside the sealing material member 30 and the separator member 31 with the members 30 and 31 abutting in an end-to-end fashion as seen in FIG. 22 and as will be further explained. After the members 30 and 31 are installed, the tube 49 is usually withdrawn. To facilitate the withdrawal, the outside of the tube 49 may be coated with a biocompatible release agent to prevent the fibrin sealing material in member 30 from sticking to the tube 49. As will become more apparent, the tube 49 may be left longer than its finished length so as to form a loading extension 58 on the projecting end 54 of the tube as shown by dashed lines in FIG. 4 and also in FIGS. 14–16. The extension 58 allows the guide tube 49 to be trimmed to length after the members 30 and 31 are preloaded into the installation assembly 12. The trailing end surface 59 on the handle 50 serves as a locating surface to help position the installation arrangement 12 in the puncture PP as will be explained.

The support mandrel 46 may be used to internally support the guide tube 48 while the members 30 and 31 are being mounted thereon as will become apparent. The support mandrel 46 is a stiff wire and is usually a metal such as stainless steel so that is does not adversely effect the members 30 and 31 nor the guide tube 48. The support mandrel 48 has an outside diameter such that it will just fit through the passage 50 in the guide tube 48 and is illustrated at about 0.033 inch. The support mandrel 48 has a length sufficiently greater than that of the guide tube 48 to permit it to project from both ends of the guide tube 48 for the support mandrel 46 to be manipulated in the guide tube.

First Embodiment of Installation Arrangement:

The first embodiment of the installation arrangement 12 is best seen in FIGS. 7–9. The installation arrangement 12 includes a delivery assembly 60 to carry the sealing material member 30 and separator member 31 and a plunger means 61 to hold the members 30 and 31 in a fixed position while the delivery assembly 60 is moved relative thereto.

The delivery assembly 60 seen in FIG. 7 includes a delivery tube 62 with a projecting leading end 64 thereon and with a pair of opposed gripping ears 65 at the opposite end thereof. The delivery tube 62 has an elongate tubular side wall 66 with central axis $A_4$. The side wall is stepped intermediate its length so as to form a thinner puncture entering section 68 adjacent the leading end 64 and a thicker base section 69 at the trailing end of the side wall 66. The puncture entering section 68 has a length $L_4$ greater than the greatest length of puncture PP likely to be encountered so that the base section 69 does not have to enter the puncture.

The side wall 64 defines a common passage 70 therethrough along the central axis $A_4$ that serves as the sealing material receiving chamber with the leading end of the passage 70 opening onto the leading end 64 of the tube 62. The passage 70 also opens onto the opposite end to the tube 62 to provide access for the plunger means 61 as will become more apparent. The diameter $D_7$ of the passage 70 corresponds to the outside diameters $D_1$ and $D_3$ of the members 30 and 31 so that they can be housed in the chamber 70 for installation in the puncture PP. In this particular illustration, the diameter $D_7$ is about 0.110 inch. The outside diameter $D_8$ of the thinner puncture entering section 68 is as small as possible while still providing sufficient strength to prevent failure of the tube 62 during use. In this particular illustration, the diameter $D_8$ is about 0.122 inch.

Any number of materials may be used to manufacture the tube 62 without departing from the scope of the invention. In this particular illustration, it is anticipated that a polymeric material will be used such as polyethylene terephthalate (PET), polystyrene or polypropylene. Where the sealing material being used is activated by exposure to radiation such as ultraviolet light, at least the puncture entering section 68 is designed to transmit the radiation therethrough. For making the tube 62 transmissive to UV light the UV blocking components usually added to the polymeric material are omitted. This allows the sealing material member to be exposed to UV light while in the passage 70.

Figure 18:
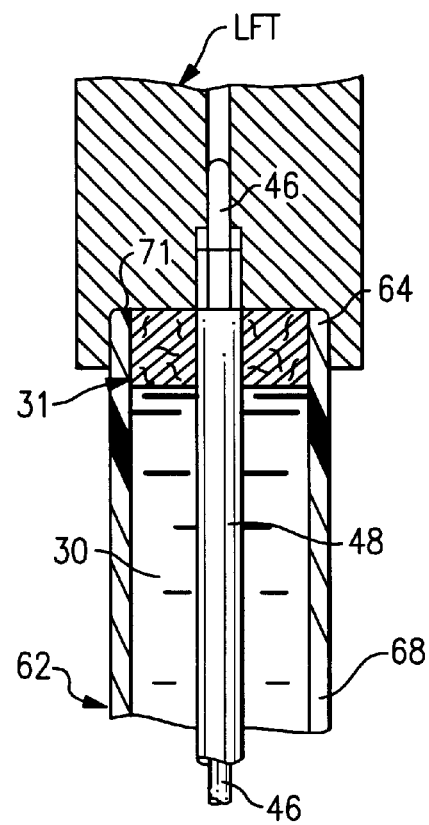
FIG. 18 is a view similar to FIG. 17 showing the retaining lip being formed in the end of the delivery assembly.

The separator member 31 is loaded into the passage 70 in the delivery tube 62 so that one end surface 42 is substantially flush with the leading end 64 on the tube 62. To assist in retaining the separator member 31 in the delivery tube 62 until it is desired to be discharged, a small inwardly turned retaining lip 71 can be formed around the inside of the leading end 64 of the tube 62 as seen in FIGS. 7 and 18 and more fully explained hereinafter.

The plunger means 61 as seen in FIG. 8 includes an elongate central support shaft 74 with a resilient sealing piston 75 on the projecting end thereof to sealingly and slidably engage the inside of the delivery tube side wall 66. The opposite end of the support shaft 74 is provided with an operating handle 76 for manually controlling the plunger means 61. The support shaft 74 defines a clearance passage 78 therethrough about the plunger central axis $A_5$ with a diameter $D_9$ selected to receive the central guide tube 48 therethrough with a clearance fit. The diameter $D_9$ illustrated is about 0.035 inch. As best seen in FIG. 8A, a central passage 79 is also defined through the sealing piston 75 with a diameter $D_{10}$ corresponding to the outside diameter $D_5$ of the central guide tube 48 so that the piston will cleanly strip the sealing material member 30 off of the central guide tube 48 when the sealing material member 30 is ejected as will become more apparent. The outside diameter $D_{11}$ of the sealing piston 75 corresponds to the inside diameter $D_7$ of the delivery tube side wall 66 to insure that the sealing material member 30 will be cleaned from the delivery tube 62 during its withdrawal from around the members 30 and 31 as will become apparent. The length of the support shaft 74 is selected so that the leading face 80 on the projecting end of the piston 75 is located a distance $L_5$ from the operating handle 76. The distance $L_5$ is selected to correspond to the overall length of the delivery tube 62 so that the face 80 on piston 75 is located substantially flush with the end 64 on the delivery tube 62 when the operating handle 76 abuts the trailing end of the delivery tube 62 as will become more apparent. Thus, the plunger means 61 can be positioned at an initial position $POS_I$ seen in FIGS. 15 and 16 to define the sealing material receiving chamber $RC_{SM}$ within the leading portion of passage 72 in the delivery tube 62. The leading most portion of the passage 72 forms the temporary holding chamber $HC_T$ for the separator member 31. When the delivery tube 62 is retracted from around the members 30 and 31 until the handle 76 on the plunger means 61 abuts the end of the delivery tube, the ejected position POSE is reached as shown in FIG. 23 where the face 80 on the piston 75 is substantially flush with the leading end 64 of the delivery tube 61.

Figure 14:
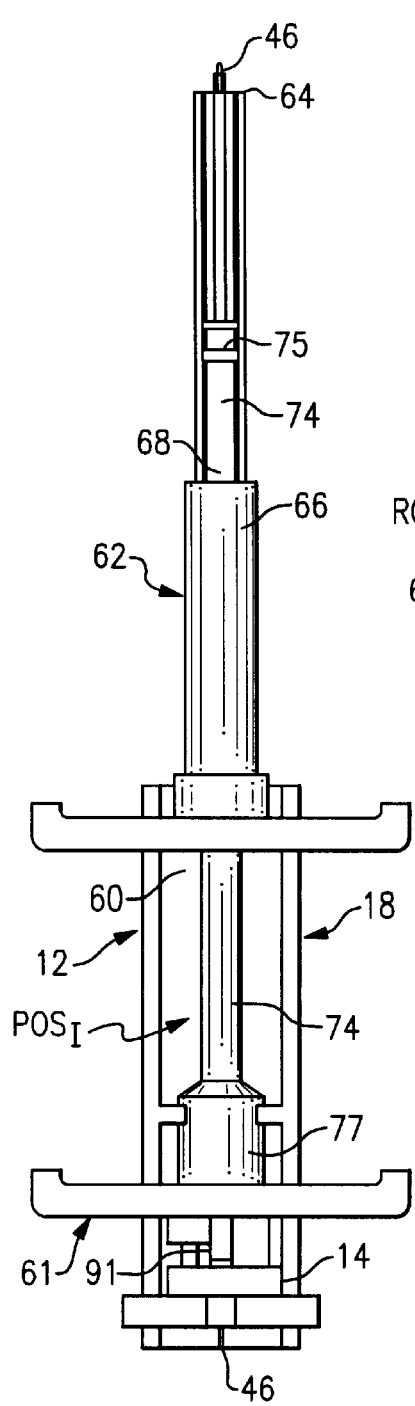
FIG. 14 is a view illustrating the delivery assembly in position to be charged with sealing material.

To prevent inadvertent discharge of the sealing material and/or separator member from the installation arrangement, an elongate U-shaped discharge prevention member 81 seen in FIG. 9 is provided for maintaining the plunger means 61 in the position POS, with respect to the delivery assembly 62. The member 81 has a central section 82 and pair of projecting legs 84. The legs 84 are generally parallel to each other and spaced apart the distance $D_{13}$ greater than the largest diameter of the plunger means or the delivery assembly but less than the overall span of the gripping ears 65 on the delivery assembly 62 or the operating handle 76 on the plunger means 61. The legs 84 define a first pair of aligned slots 85, therein for receiving the gripping ears 65 on the delivery assembly 62, a second pair of aligned slots 85₂ therein for receiving the operating handle 76 on the plunger means 61, and a third pair of aligned slots 85₃ therein for receiving the wings 55 on the positioning handle 50 of the guide tube assembly 48. The spacing distance $D_{s1}$ between the slots $85_1$ and $85_2$ is selected to maintain the plunger means 61 in the initial position $POS_I$ with respect to the delivery tube 62 as seen in FIGS. 14 and 21. The slots $85_3$ are spaced from the slots $85_2$ the distance $D_{S2}$ to keep the forward edge 56 on the guide tube assembly 48 abutting the trailing end of the installation assembly 12 so that the guide tube 49 is positively located in the delivery tube 62. To provide clearance for the locking means on the installation arrangement 12 as will become more apparent, a clearance cutout 86 is provided in one of the legs 84 as seen in FIGS. 1 and 14.

To keep the member 81 in place, a clip section 88 may be provided inside the member 81 to resiliently engage the boss 77 on the handle 76 as seen in FIG. 1. Likewise, a safety pin 89 may be removably mounted in the member 81 through the legs 84 to positively lock the prevention member 81 onto the delivery assembly 60. The safety pin 89 would be removed only when the physician is ready to retract the delivery tube 62 from around the fibrin member 30. To remove the prevention member 81, the operator removes the safety pin 89 and pulls the member away from the plunger member 61 to snap the clip section 88 off of the boss 77.

The interconnect means 14 includes locating means 90 that allows the installation arrangement 12 to be accurately positioned relative to the temporary sealing arrangement 11. The interconnect means 14 also includes locking means 91 for positively fixing the plunger means 61 on the installation arrangement 12 relative to the control means 20 of the temporary sealing arrangement 11 so that the sealing material can be accurately located within the puncture PP.

The locating means 90 includes first indicia $IND_1$ and second indicia $IND_2$ on the catheter control tube 20 as seen in FIG. 2. The first indicia $IND_1$ can be used with the locating end surface 59 on the trailing end of the central guide tube assembly 48 to locate the installation arrangement 12 on the control member 20 as will become more apparent. As an alternative, the second indicia $IND_2$ can be used with the locating end surface 96 seen in FIGS. 1, 14 and 21 on the trailing end of the locking means 91 if the central guide tube assembly 48 is not used to locate the installation arrangement 12 on the control member 20. To indicate when it is safe to remove the guide tube assembly 48 after the sealing material is installed, a safety indicia band $IND_2$ is provided as seen in FIG. 2.

Figure 10:
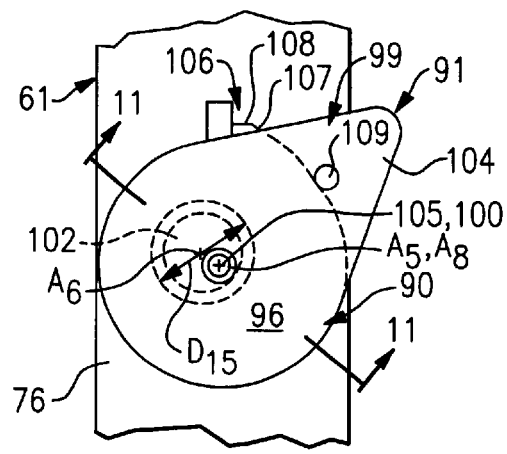
FIG. 10 is an enlarged end view of the interlock means of the locating means of the invention in the release position.
Figure 11:
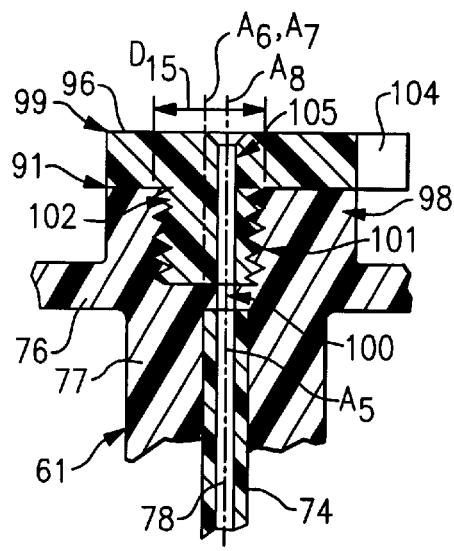
FIG. 11 is a cross-sectional view taken along line 11—11 in FIG. 10.

The locking means 91 is mounted on the trailing end of the plunger means 12 at the operating handle 76 as best seen in FIGS. 8 and 10–13. The locking means 91 includes a base member 98 in the form of a cylindrical boss fixedly mounted on the trailing end of the plunger means 12 and a lock member 99 operatively associated with the base member 98 to engage the guide tube 49 and control member 20 to selectively and releasably lock the plunger means 12 and the guide tube assembly 48 with respect to the control member 20. The base member 98 defines a central receiving passage 100 therethrough centered on the central axis $A_5$ of the plunger means 12 and in axial registration with the central passage 78 through the plunger means as best seem FIG. 11. The diameter of the receiving passage 100 corresponds to that of clearance passage 78 through the support shaft 74 to freely receive the guide tube 49 and control member 20 therethrough. The base member 98 also has an enlarged passage 101 therein with a central axis $A_6$ parallel to the central axis $A_5$ of the receiving passage 100 but shifted laterally thereof. The enlarged passage 101 has a diameter $D_{15}$ sufficiently larger than the diameter of the passage 100 so that, when the passages 100 and 101 are arranged end-to-end as seen in FIG. 11, the passage 100 will open into the passage 101. The passage 101 is internally threaded for use with the lock member 99 as will become more apparent.

Figure 12:
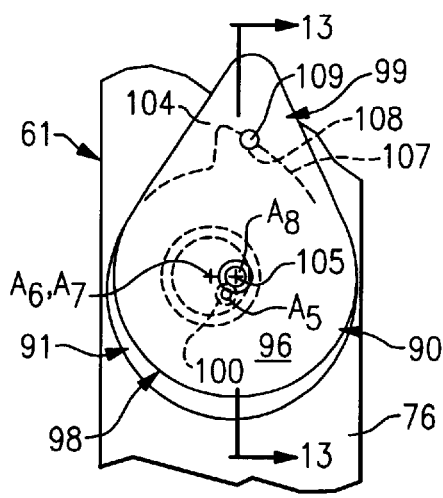
FIG. 12 is an enlarged end view of the interlock means of the locating means of the invention in the locking position.
Figure 13:
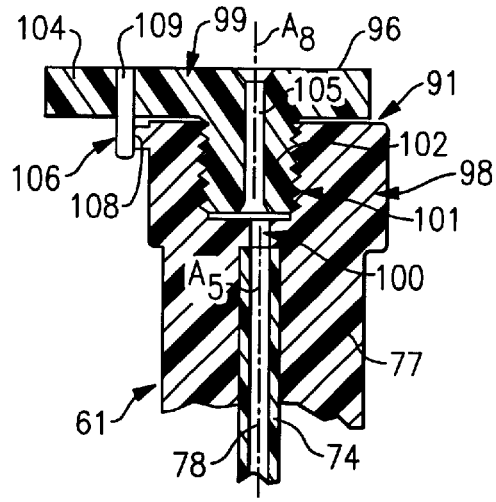
FIG. 13 is a cross-sectional view taken along ling 13—13 in FIG. 12.

The lock member 99 has an externally threaded projection 102 with central axis $A_7$ sized to be threadedly screwed into the enlarged passage 101. The member 99 also has an eccentric handle 104 integral with one end of the projection 102 so that a portion thereof projects laterally outwardly from the projection 102. The lock member 99 defines a locking passage 105 therethrough about axis $A_8$ sized to slidably receive the guide tube 49 and the control member 20 therethrough. The axis $A_8$ is laterally offset from the central axis $A_7$ by the same distance as the offset between the receiving passage axis $A_5$ and the enlarged passage axis $A_6$ in the base member 98 so that, at one rotational position of the lock member 99 relative to the base member 98, the locking passage 105 is in registration with the receiving passage 100 in the base member 98 as seen in FIGS. 10 and 11. As the member 99 is rotated in the member 98, the passages 100 and 105 move out of registration as seen in FIGS. 12 and 13 to tightly clamp the control member 20 and the guide tube 48 between the members 98 and 99. The ends of the passages 100 and 105 at their common interface are rounded to prevent the tube 48 or control member 20 from being cut. Thus, the locking member 99 is movably mounted on the base member 98 so that the locking passage 105 can be moved from the release position seen in FIGS. 10 and 11 in which the locking passage 105 is in axial alignment with base receiving passage 100 so that the control member 20 and guide tube 48 can freely move in both the receiving and locking passages 100 and 105 to a locking position seen in FIGS. 12 and 13 in which the locking passage 105 is out of axial alignment with the base receiving passage 100 so that the control member 20 and guide tube 48 will be gripped between the base and locking members 98 and 99 to fixedly hold the control member 20 relative to the base and locking members 98 and 99 and thus the plunger means 61 and guide tube assembly 48 relative to the temporary sealing arrangement 11. While the clip member 81 is maintaining the relative position between the delivery tube 62 and plunger means 61, this fixes the position of the delivery tube 62 relative to the control member 20. This arrangement permits locking the installation arrangement 12 to the temporary sealing arrangement 11 without axial movement between the control member 20 and the installation arrangement during locking. While a specific construction has been shown and described for illustration purposes, it will be understood that any mechanism can be used as long as a cam locking member is used to exert a sidewise force on control member 20.

In order to maintain the lock member 99 in a locking position, a catch means 106 seen FIGS. 10 and 12 is provided to releasably hold the handle 104 in position clamping the guide tube 49 and the control member 20. The catch means 106 includes a cam 107 with notch 108 on the base member 98 and a detent pin 109 on handle 104 that cooperate to hold the handle 104 in a fixed rotational position when the pin 109 is forced into the notch 108. The resiliency of the pin 109 and the cam 107 is such that the handle 104 can be rotatably forced in the opposite direction to release the handle 104 for rotation to release the guide tube 48 and control member 20. It will be appreciated that the control member 20 will be clamped by the locking means 91 if the guide tube 48 is not present.

Preparation of First Embodiment of Installation Arrangement:

The preparation of the installation arrangement 12 for use will be described using frozen fibrin although different techniques may be used for different sealing materials. Likewise, different techniques may be used depending on thee whether the sealing material is in a solid or liquid state.

Figure 15:
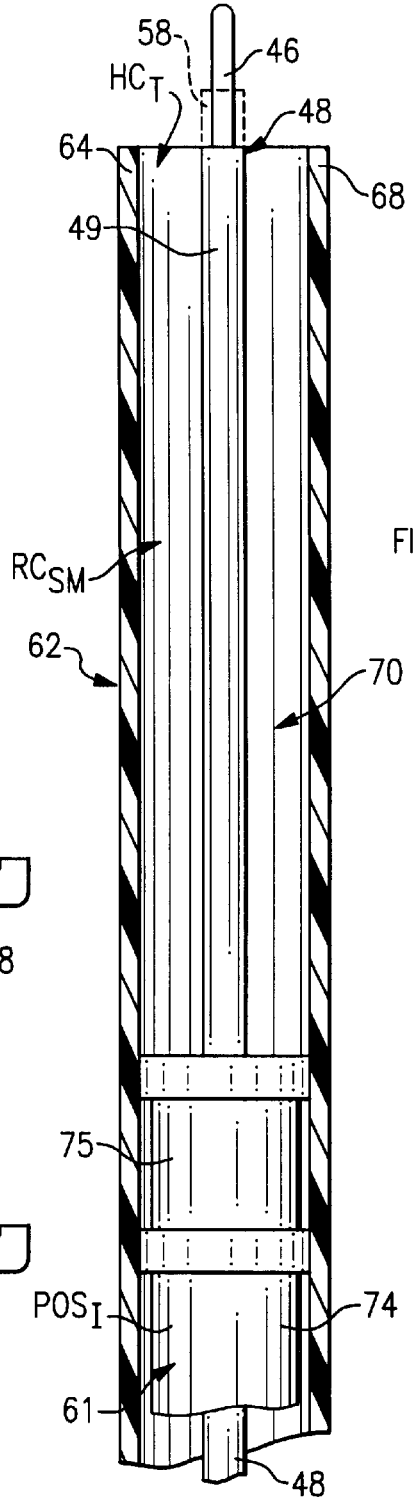
FIG. 15 is an enlarged longitudinal cross-sectional view of the sealing material holding chamber in the delivery assembly seen in FIG. 14.

The fibrin member 30 may be formed in situ in the installation arrangement 12 as shown in FIGS. 14–18. The delivery assembly 60 is assembled to the initial position POS, as seen in FIGS. 14 and 15. When the support mandrel 46 is used, it is inserted through the central guide tube 49 so that it projects out of the ends of the guide tube 49 and the thus assembled internal guide arrangement 45 inserted through the central passage 78 through the support shaft 74 on the plunger means 61 and the central passage 79 through the piston 75 on the end of the support shaft 74 until the leading edge 56 on the guide tube assembly 48 abuts the trailing end surface 96 on the locking means 91. If the guide tube 49 is precut to length, the projecting end 54 thereon will be flush with the projecting end 64 on the delivery tube 62. Where the guide tube 49 purposely left long as seen by dashed lines in FIG. 15, the extension 58 will project out of the projecting end 64 of the delivery tube 62. The discharge prevention member 81 is then installed to hold the guide tube assembly 48, the plunger means 61, and the delivery assembly 60 in the initial position POSE. The safety pin 59 is installed in the member 81 to hold the arrangement together. This is the position seen in FIGS. 14 and 15 with the support mandrel being used.

Figure 16:
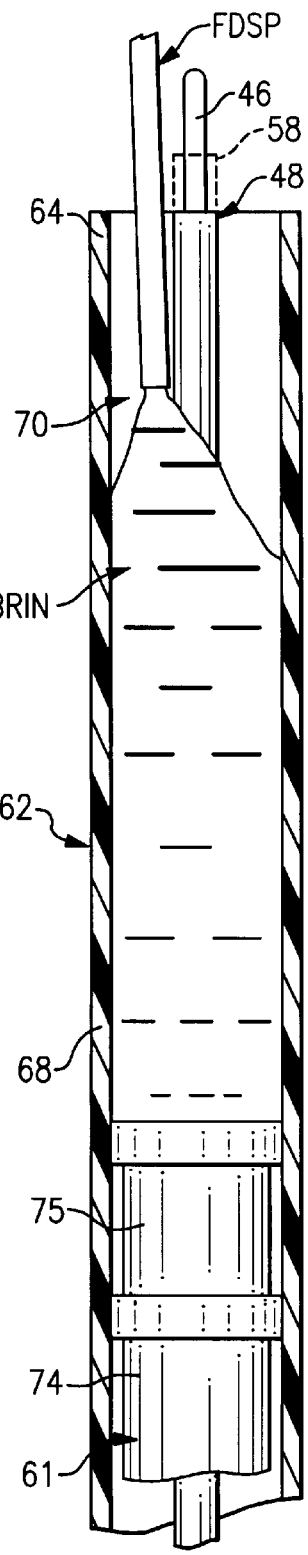
FIG. 16 is a view similar to FIG. 15 showing the sealing material being loaded into the delivery assembly.

The fibrin in a flowable state is then injected into the thusly formed sealing material holding chamber $RC_{SM}$ as seen in FIG. 16 using a convenient dispenser FDSP with a discharge spout that will fit through the upturned open end of passage 70 at the projecting end 64 of the delivery tube 62 and around the guide tube 46. If the extension 58 is left on the guide tube 49, it serves as a guide for the dispenser tip on the of the dispenser FDSP. If the support mandrel 46 is being used, the end of the mandrel projecting from the projecting end 64 on the tube 62 also serves as a guide for the dispenser tip and also fills the inside of the guide tube 48. This serves to prevent the sealing material from being inadvertently deposited inside the guide tube so as to interfere with the passage of the control member 20 of the temporary sealing arrangement 11 therethrough.

Figure 17:
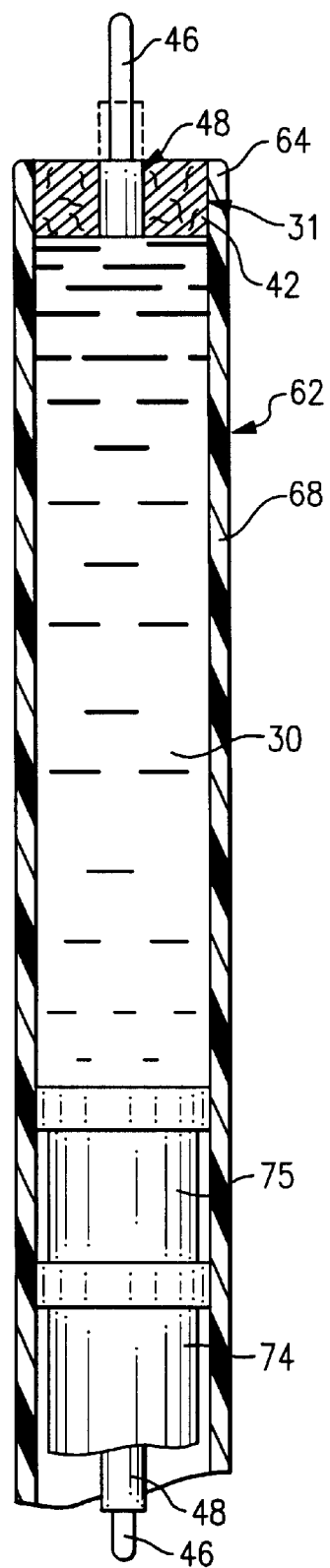
FIG. 17 is a view similar to FIG. 16 showing the separator member loaded into position in the delivery assembly.

When the fibrin has filled the chamber $RC_{SM}$ to the correct level, the preformed separator member 31 is fed over the mandrel 46 and the end of the guide tube 48 until it enters the open end of the delivery tube 62 and is flush with the projecting end 64 of the tube 62 as seen in FIG. 17. When the separator member 31 is made of collagen, that end face 42 in contact with the fibrin may be overcoated with a bioabsorbable membrane to keep the flowable fibrin from starting the collagen from prematurely activating.

To maintain the integrity of the thusly positioned separator member 31 and flowable fibrin 30, the lip 71 is formed by using a forming tool LFT seen in FIG. 18. The tool LFT is appropriately heated and brought into contact with the projecting end 64 of the delivery tube 62 to nonelastically deform the end 64 and form the lip 71 as seen in FIGS. 18 and 19.

If the guide tube 49 has been left with the extension 58 while the fibrin sealing material and the separator member 31 are installed, the extension 58 is trimmed off so that the thusly formed projecting end 54 of the tube 49 is flush with the end of the tube 62 as seen in FIG. 22. If the guide tube 49 is initially formed to length, the projecting end 54 will already be present.

After this is complete, the entire precharged delivery assembly 60 is placed in a freezer to freeze the flowable fibrin into the frozen fibrin member 30 that can be discharged into the puncture PP as will become apparent. As a matter of fact, the assembly 60 may be placed in the sterilized packaging SP before it is frozen so that it is ready to use.

When the fibrin member 30 is preformed in a separate molding arrangement, it is prefrozen. The guide tube assembly 48 is inserted into the plunger means 61 as seen in FIG. 19. One way to load the members 30 and 31 is to load them over the projecting end of the guide tube 49 with the support mandrel 46 inserted through the guide tube. The thusly loaded guide tube assembly 48 and plunger means 61 are inserted into the passage through the delivery assembly 60 from the trailing thereof until the leading end surface 42 on the member 31 is flush with the leading end 64 of the delivery tube 62 as seen in FIG. 21. The support mandrel 46 is then removed and the discharge prevention member 81 installed to hold the parts in place. The thusly charged installation arrangement 12 is then returned to the freezer until its use is required.

Alternatively, the guide tube assembly 48 inserted into the plunger means 61 as seen in FIG. 19 can be inserted into the delivery assembly 62 as seen in FIG. 20 and the frozen member 30 and separator member 31 loaded over the guide tube 49 and into the delivery tube 62 from the projecting ends thereof. Thereafter, the lip 71 can be formed in the end 64 of the delivery tube 62 to produce the charged installation arrangement 12 seen in FIG. 21.

Method of Use

Just before the procedure, the delivery assembly 62 is removed from the freezer so that the fibrin member 30 starts to thaw. The thawing is timed so that the fibrin member 30 will have sufficient integrity for it to be installed as a substantially solid member. Where the fibrin in member 30 is activated by irradiation such as UV light, it can be done through the tube side wall 66 of the delivery tube 62 at this time or just before it is installed in the puncture. The thawing time and irradiation exposure will depend on the particular formulation of fibrin used in the sealing process.

The method of sealing a blood vessel using the first embodiment of the invention is illustrated in FIGS. 24–30. As seen in FIG. 24, the projecting end 22 on the control member 20 of the temporary sealing arrangement 11 is preinstalled while the introducer guide sheath GS is still in position. The projecting end 22 on control member 20 is fed down through the guide sheath GS and into the blood vessel lumen BVL by the physician. The control member 20 is threaded through the guide sheath GS until the collapsed tamponading member 21 passes into the blood vessel lumen BVL as seen in FIG. 24. At this time, the coupling 25 is not being used so that the guide sheath GS is removed from the puncture PP over the trailing end 24 of the leading portion of the control member 20. After the guide sheath GS is removed, the precharged delivery assembly 60, which has been removed from the sterile packaging SP, is installed over the exterior end 24 of the control member 20 with the leading end 64 on the delivery tube 62 facing the skin SK of the patient as seen in FIG. 25. For this installation, the control member 20 is threaded through the guide tube 49 so as not to disturb the separator member 31 or the fibrin member 30. Thereafter, the coupling 25 is used to connect the leading and trailing portions of the control member 20 as seen in FIG. 25 and the tamponading member 21 expanded to its expanded condition with the syringe 26.

Figure 27:
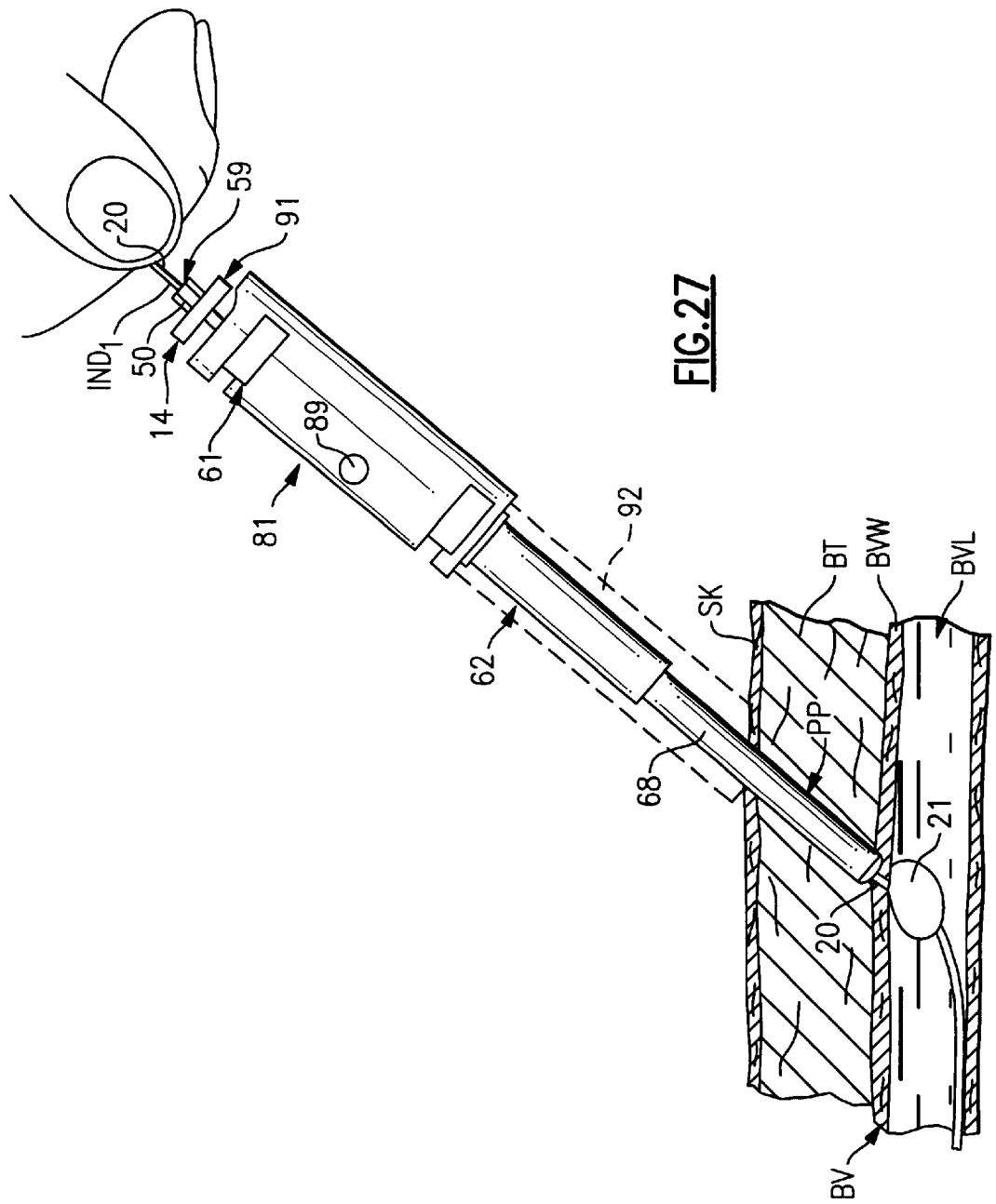

The physician then physically pulls back on the control member 20 so that the expanded tamponading member 21 is pulled back up against the inside end of the puncture PP through the blood vessel wall BVW as seen in FIG. 27. After the tamponading member 21 is pulled up against the inside end of the puncture PP, the physician pushes the delivery assembly 60 toward the patient so that the delivery tube 62 passes into the puncture PP. While still holding the tamponading member 21 up against the inside end of the puncture PP, the physician continues to carefully push the delivery assembly 62 toward the patient while holding the control member 20 to keep the tamponading member 21 in place until the first indicia $IND_1$ just becomes visible at the trailing end 59 of the guide tube assembly 48 as seen in FIG. 27. The trailing end of the discharge prevention member 81 has been broken away in FIG. 27 so that the trailing end surface 59 on the handle 50 of the guide tube assembly 48 and the indicia $IND_1$ is visible. At this time, the physician knows exactly where the projecting end 64 of the delivery assembly 60 is located in the patient. This is because the indicia is located a distance from that side of the tamponading member 21 abutting the blood vessel wall BVW equal to the length $L_{30A}$ of the guide tube assembly 48 plus the average thickness of the blood vessel wall BVW likely to be encountered in the particular application. Since this locates the projecting end 64 of the delivery assembly 60 immediately outside the blood vessel wall BVW and since the leading end surface 42 is flush with the projecting end 64 of the delivery assembly 60, the physician thus accurately locates the separator and fibrin members 31 and 30 immediately outside the blood vessel wall BVW to insure that these members will not inadvertently protrude through the blood vessel wall. Moreover, the tamponading member 21 is centered in the end of the puncture PP and holds the puncture through the blood vessel wall BVW closed. The thusly positioned delivery assembly 60 is illustrated in FIG. 27. Once the delivery assembly 60 is in position, the physician manipulates the lock member 99 of the locking means 91 to fix the plunger means 61 on the delivery assembly with respect to the control member 20. This serves to positively interconnect the delivery assembly 60 with respect to the blood vessel end of the puncture PP. This position can be maintained by the physician continuing to pull back on the control member 20 to keep the tamponading member 21 up against the blood vessel wall or a skin locating arrangement 92 indicated by dashed lines in FIG. 27 such as that shown and described in copending application Ser. No. 07/817,587 mounted on the plunger means 61 may be deployed down against the patient's skin SK to hold the assembly 60 in place. It will be appreciated that the leading face 80 on the plunger means 61 is fixed relative to the blood vessel wall BVW.

Figure 28:
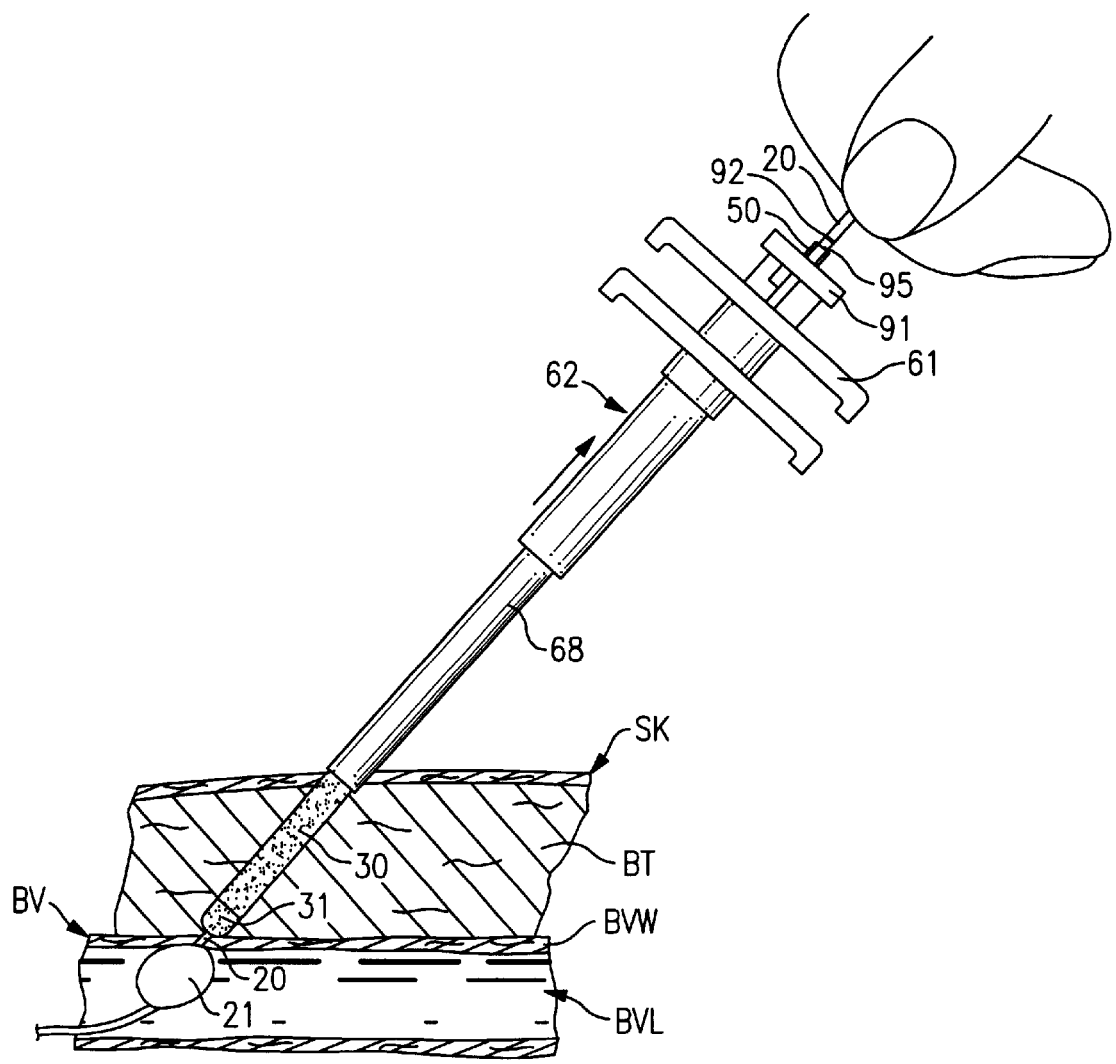

The physician then removes the discharge prevention member 81 so that the delivery tube 62 can be moved relative to the plunger means 61. The physician pulls back on the gripping ears 65 on the tube 62 to move it out of the puncture while the locking means 91 holds the plunger means 61 fixed relative to the control member 20 and the end of the puncture PP at the blood vessel wall as shown in FIG. 28. The plunger means 61 serves to hold the separator member 31 and the fibrin member 30 in place as the delivery tube 62 is retracted from around the members 31 and 30. Thus, the separator member 31 and the fibrin member 30 are left in the puncture PP in the proper position for sealing. The separator member 31 almost immediately starts forming a coagulum immediately outside of the blood vessel wall and the activated fibrin member 30 starts bonding to the body tissue at the puncture interface.

Figure 29:
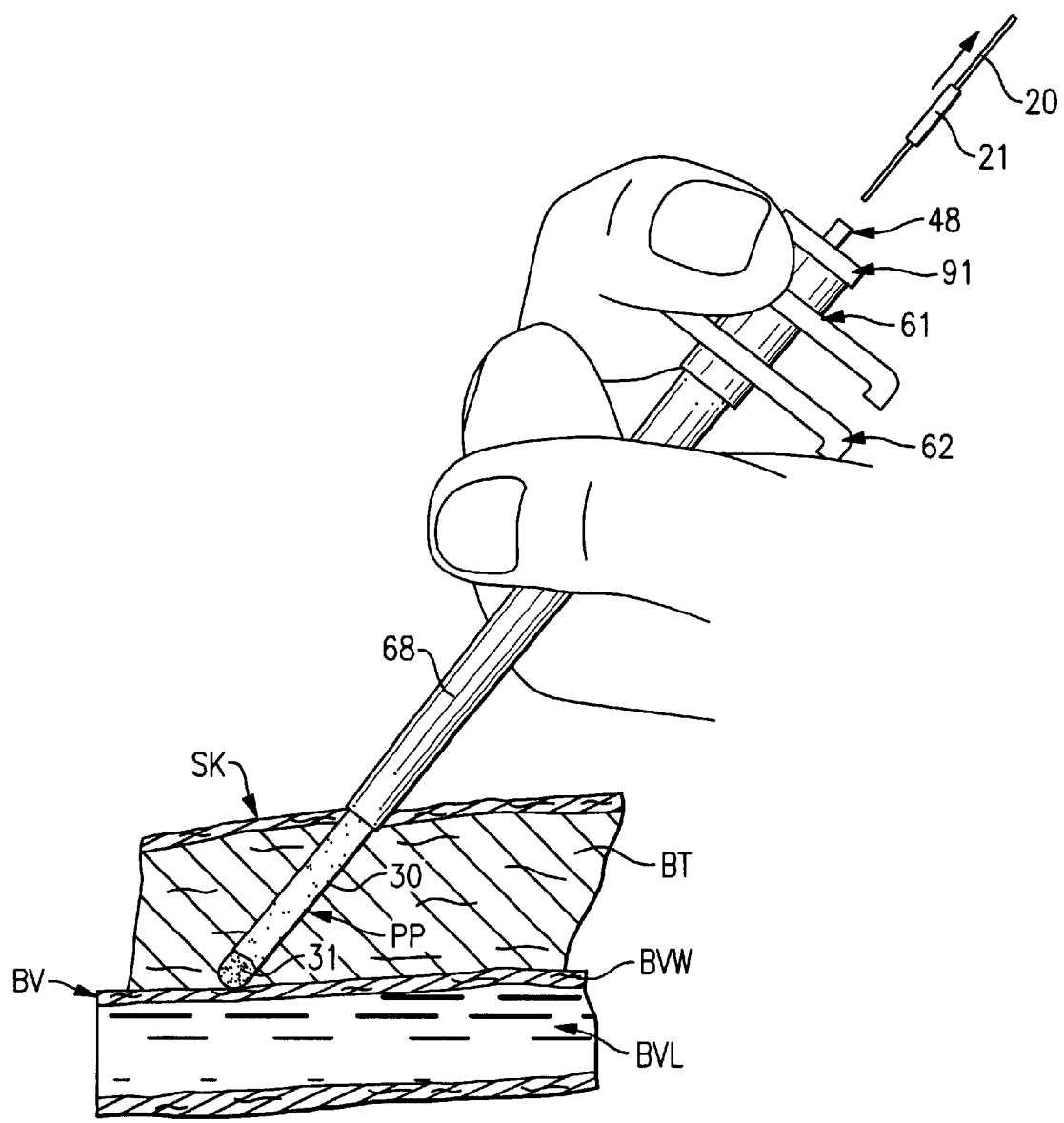

When the members 31 and 30 have substantially sealed the puncture PP, the physician unlocks the locking means 91 to release the assembly 60 from the control member 20 and collapses the balloon 21. While manually maintaining the delivery assembly 60 in position at the end of the puncture PP, the physician carefully retracts the control member 20 and collapsed balloon 21 at least up into the guide tube 49 until the safety indicia $IND_S$ is visible at the end of the guide tube assembly 48 indicating that the member 21 is within the tube 49. The members 20 and 21 may be completely removed through the guide tube 49 to remove the temporary sealing arrangement 11 from the patient as shown in FIG. 29.

Figure 30:
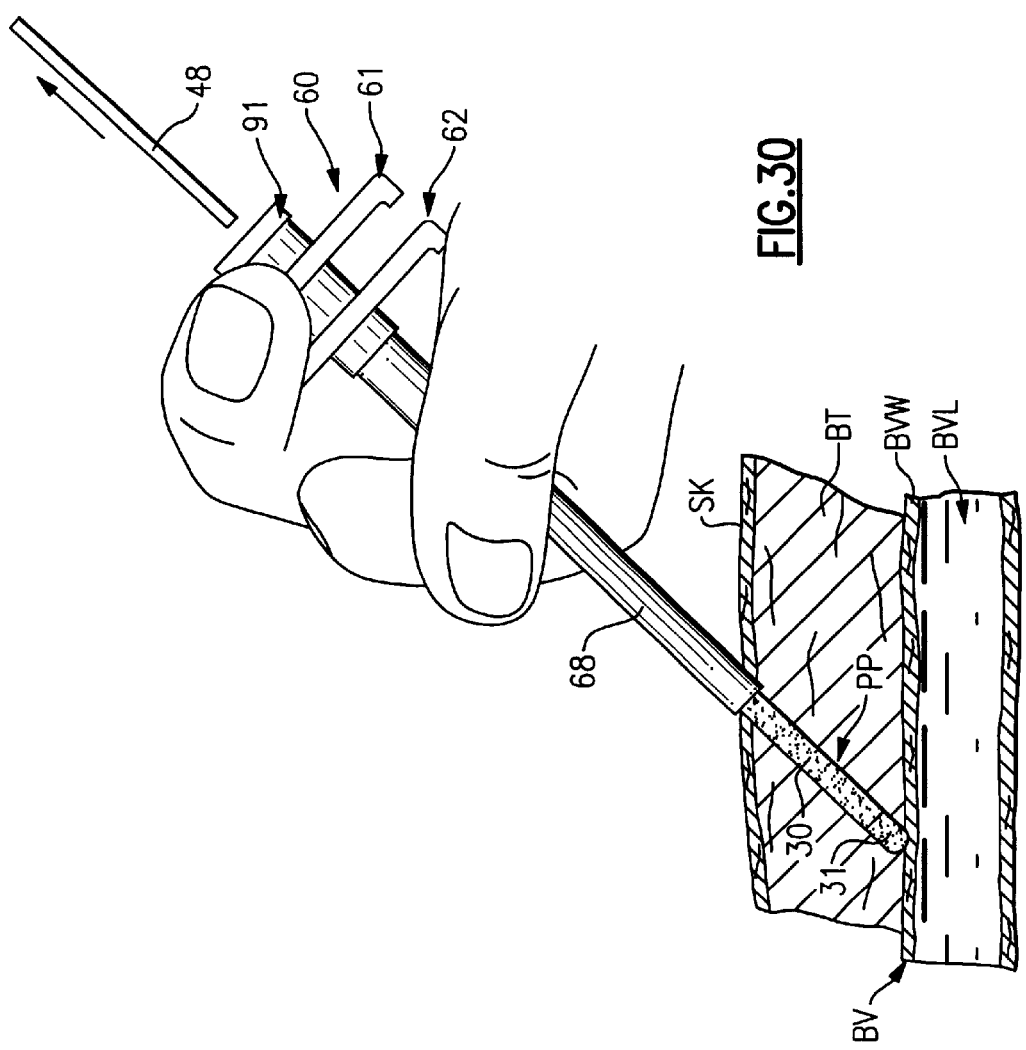

While the physician continues to hold the delivery assembly 60 in place, the guide tube 49 is withdrawn through the plunger means 61 while the sealing piston 75 holds the fibrin member 30 and thus the separator member 31 in position in the puncture PP as seen in FIG. 30. Preferably, the outside of the guide tube 49 will be coated with a biocompatible release agent to insure that the collagen in member 31 and the fibrin in member 30 will cleanly separate from the guide tube 30 as it is withdrawn. The close fit between the guide tube 48 and the piston 75 assures that none of the collagen or fibrin is withdrawn on the guide tube 49. The passages through the separator member 31 and fibrin member 30 collapse as the guide tube 49 is withdrawn to complete the seal. The physician then removes the delivery assembly 60 to complete the process.

It will be understood that the particular sequence of steps used in the sealing process may be varied depending on the circumstances. For instance, in some applications, it may be desirable to remove the guide tube 49 along with the collapsed balloon 21 or to remove the guide tube before the removal of the collapsed balloon 21. In some instances, it may be difficult to remove the guide tube 49 and it may be left in place and cut off at the skin surface provided it is made out of a biocompatible material or a bioabsorbable material. If the guide tube 49 is left in place, the passage 50 through it is so small, the blood will quickly form a coagulum in the leading end thereof to seal it.

Second Embodiment of Installation Arrangement:

The second embodiment of the installation arrangement designated 112 is best seen in FIGS. 31–40. The installation arrangement 112 is designed to place a flowable sealing material 130 into the puncture PP and uses the separator member 31 to separate the flowable sealing material 130 from the blood vessel wall and the end of the puncture opening into the blood vessel lumen BVL. The installation arrangement 112 includes a sheath assembly 140 into which a delivery assembly 160 carrying the sealing material 130 and separator member 31 is slidably mounted, and a plunger means 161 to hold the material 130 and member 31 in a fixed position while the delivery assembly 160 is moved relative thereto and while the sheath assembly 140 is moved relative to the delivery assembly 160 as will become more apparent.

Figure 31:
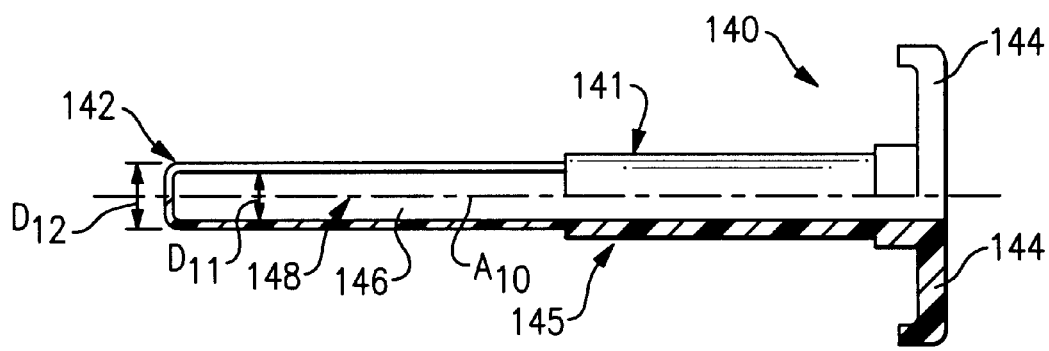
FIG. 31 is a side view of the sheath member of a second embodiment of the installation arrangement of the invention shown in half section.

The sheath assembly 140 seen in FIG. 31 includes a sheath tube 141 with a projecting leading end 142 thereon and with a pair of opposed gripping ears 144 at the opposite end thereof. The sheath tube 141 has an elongate tubular side wall 145 with central axis $A_{10}$. The side wall is stepped intermediate its length so as to form a thinner puncture entering section 146 adjacent the leading end 142 and a thicker base section at the trailing end of the side wall 145. The puncture entering section 146 has a length greater than the greatest length of puncture PP likely to be encountered so that the base section does not have to enter the puncture. The side wall 145 defines a common passage 148 therethrough along the central axis $A_{10}$ that serves as the sealing material receiving chamber with the leading end of the passage 148 opening onto the leading end 142 of the tube 141. The passage 148 also opens onto the opposite end of the tube 141 to provide access for the delivery assembly 160 as will become more apparent. The diameter $D_{11}$ of the passage 148 corresponds to the outside diameter of the delivery assembly 160 so that it can be inserted into the passage 148 for installation in the puncture PP. The outside diameter $D_{12}$ of the thinner puncture entering section 146 is as small as possible while still providing sufficient strength to prevent failure of the sheath tube 141 during use. In this particular illustration, the diameter $D_{12}$ is about 0.122 inch. The sheath tube 141 is usually made out of material similar to that of the delivery tube 62 in the first embodiment of the invention. Where the sealing material being used is activated by exposure to radiation such as ultraviolet light, at least the puncture entering section 146 is designed to transmit the radiation therethrough like section 68 in the first embodiment of the installation arrangement 12.

Figure 32:
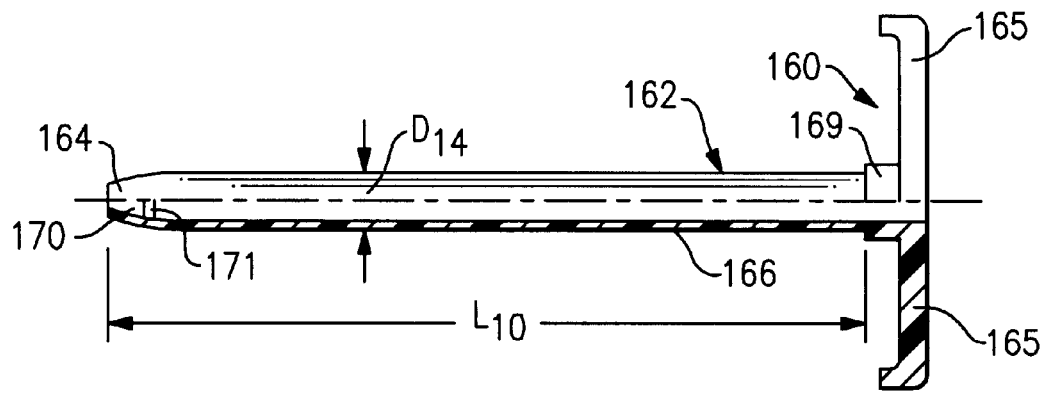
FIG. 32 is a side view of the delivery member of the second embodiment of the installation arrangement of the invention.
Figure 33:
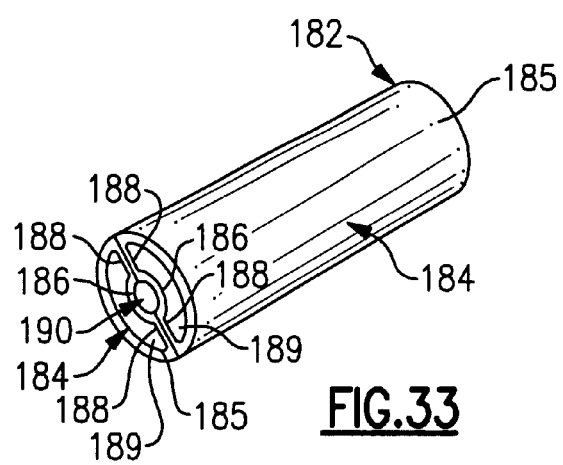
FIG. 33 is a perspective view of the material carrying capsule for the second embodiment of the installation arrangement.

The delivery assembly 160 seen in FIGS. 32 and 35 includes delivery tube 162 with a projecting leading end 164 thereon and with a pair of opposed gripping ears 165 at the opposite end thereof. The delivery tube 162 has an elongate tubular side wall 166 with an outside diameter $D_{14}$ corresponding to that of the passage 148 so that the tube 162 will be slidably received in the passage 148 in the sheath tube 141. An annular abutment boss 169 is provided adjacent the ears 165 to engage the trailing end of the sheath member 140 and act as a stop for the assembly 160 projecting into the sheath assembly 140. The projection length $L_{10}$ of the side wall 166 is selected to locate the projecting end 164 inboard of the projecting end 142 of the sheath tube 141 a distance corresponding to the thickness of the separator member 31 as seen in FIG. 35. The leading end portion of the tube 166 defines a mixing chamber 170 therein whose trailing end is defined by an annular abutment flange 171 projecting inwardly from the side wall 166 and defining a discharge opening 172 therethrough as best seen in FIGS. 35 and 36. Mixing agitator vanes 173 are provided in chamber 170 to mix the sealing material as will become more apparent. An ampule receiving chamber 181 is defined on the trailing side of the abutment flange 171 whose trailing end is closed by the plunger means 161.

The plunger means 161 corresponds to the means 61 of the first embodiment of the invention except that the discharge piston 175 is rigid and defines an outwardly flaring leading face 180 thereon. The central support shaft 174 corresponds to that of the first embodiment.

While the fibrin sealing material 130 may be a single or multiple component composition, it is illustrated as a two component material in the drawings for simplicity without limitation of the intended coverage. The uncured sealing material 130 is carried in a multiple compartment ampule 182 seen in FIGS. 33, 35 and 37. The ampule 182 includes a pair of flexible compartment side walls 184 arranged to form a semi-cylindrical shaped material carrying chamber MCC therein. The side walls 184 each have an outer semiannular section 185 and an inner semiannular section 186 with their edges joined by radially extending sections 188. The sections 188 of the two side walls 184 lie in juxtaposition with each other but are not attached to each other except along the outermost edges so that the sections 186 and 188 can be folded outwardly against the section 185. Opposite ends of the semi-cylindrical shaped material carrying chambers MCC are closed by rupturable seals 189. The ampule 182 thus defines a central passage 190 therethrough between the two chambers MCC to receive the guide tube 49 of the guide tube assembly 48 therethrough and also allow the forwardmost end of the piston 175 will fit into the trailing end of the ampule 182 as seen in FIG. 35.

The two liquid components of the sealing material 130 are loaded into the different chambers MCC so that the ampule can be stored. When the physician is ready to install the material, the ampule 182 is dropped into the delivery assembly 160 from the trailing end thereof and the plunger means 161 inserted into the delivery assembly 162 behind the ampule 182 as seen in FIG. 35. The guide tube assembly 48 is then installed through the plunger means 161 and the ampule 182. This arrangement is then installed into the sheath tube 141. If the lip 149 is preformed on the leading end 142 on the sheath tube 141, the separator member 31 is fitted over the projecting end of the guide tube 48 and then inserted along the passage 148 in the sheath tube 141 until the leading end surface 42 abuts the lip 171 and is flush with the end of the tube 141 as seen in FIG. 35. If the lip 149 is formed with the tool LFT after the separator member 31 is loaded into the sheath assembly 140, the member 31 can be loaded from the projecting end 142 on the sheath assembly 140 after the delivery assembly 161 is positioned in the sheath assembly 141.

After the sealing material ampule 182 is loaded, a discharge prevention member 191 similar to the member 81 of the first embodiment is installed as seen in FIG. 34. The member 191 has four sets of slots 192 therein; one set 192, for the ears 144 on the sheath assembly 140, one set 192₂ for the gripping ears 165 on the delivery assembly 160, one set 192₃ for the handle 176 on the plunger means 161, and one set 192₄ for the handle 50 on the guide tube assembly 48. The slots 192₂ are elongate so that the delivery assembly 160 can be retracted toward the handle 176 on the plunger means 161 but a pair of subslots 193 are provided in the base of the slots 192₂ to receive a secondary locking member 196 to hold the delivery assembly 160 in its extendedmost position seen in FIG. 34 until the physician is ready to retract the assembly 160. The slot 194 is also provided for clearance of the locking means 91 on the plunger means 161. A removable safety pin 195 is provided to hold the member 191 in place.

Use of Second Embodiment of Installation arrangement:

The second embodiment 112 of the installation arrangement is also used with the temporary sealing arrangement 11. The temporary sealing arrangement 11 is installed like the first embodiment of the installation arrangement as seen in FIG. 24. The guide sheath GS is removed and the precharged installation arrangement 112 slipped over the control member 20 like the first embodiment as seen in FIGS. 25 and 26. The physician inflates the balloon 21 and pulls back on the control member 20 to locate the balloon 21 at the end of the puncture PP opening into the blood vessel BV and pushes the second embodiment into the puncture like the first embodiment to the position illustrated in FIG. 27 for the first embodiment.

Figure 39:
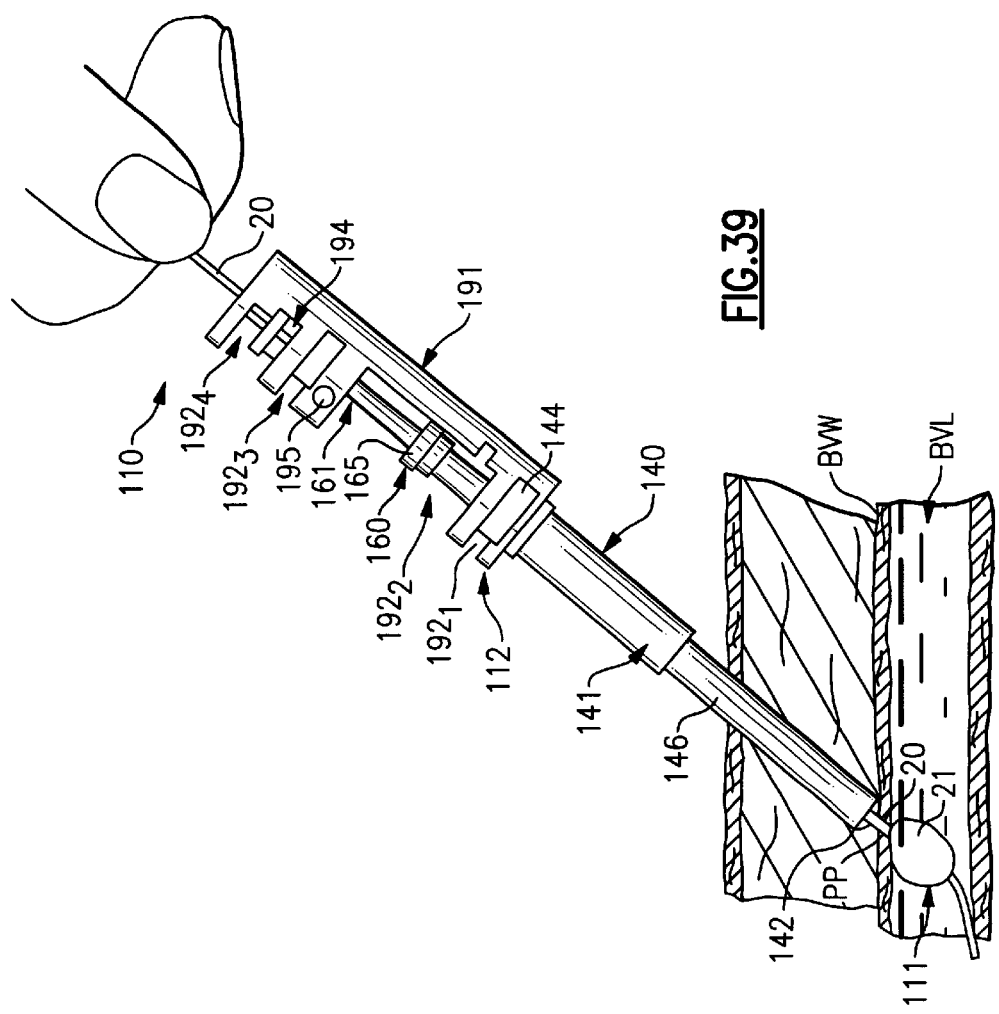
FIG. 39 illustrates the delivery tube assembly retracted in the second embodiment of the invention as it is being installed.

The physician then removes the secondary locking member 196 and starts to retract the delivery assembly 160 as seen in FIGS. 38 and 39 while the discharge prevention member 191 continues to hold the sheath assembly 140 in its forwardmost position. This forces the ampule 182 over the piston 175 to cause it to extend between the two side walls 184 of the ampule 182. This forces the inner semiannular sections 186 and the radially extending sections 188 out toward the respective outer semiannular sections 185 to which they are connected as best seen in FIG. 38. The liquid components $130_A$ and $130_B$ of the fibrin sealing material is thus forced toward the projecting end of the ampule 182 to rupture the leading end seal 189 and discharge the components $130_A$ and $130_B$ through the mixing chamber 170 to mix same and into the space behind the separator member 31 formed in the sheath tube 141. When the delivery assembly 160 is fully retracted back against the plunger means 61, the sealing material 130 will fill the delivery tube 162 around the guide tube 49 between the end of the delivery tube 162 and the separator member 31. The mixing of the components of the sealing material 130 activates the material to start the sealing process.

Figure 40:
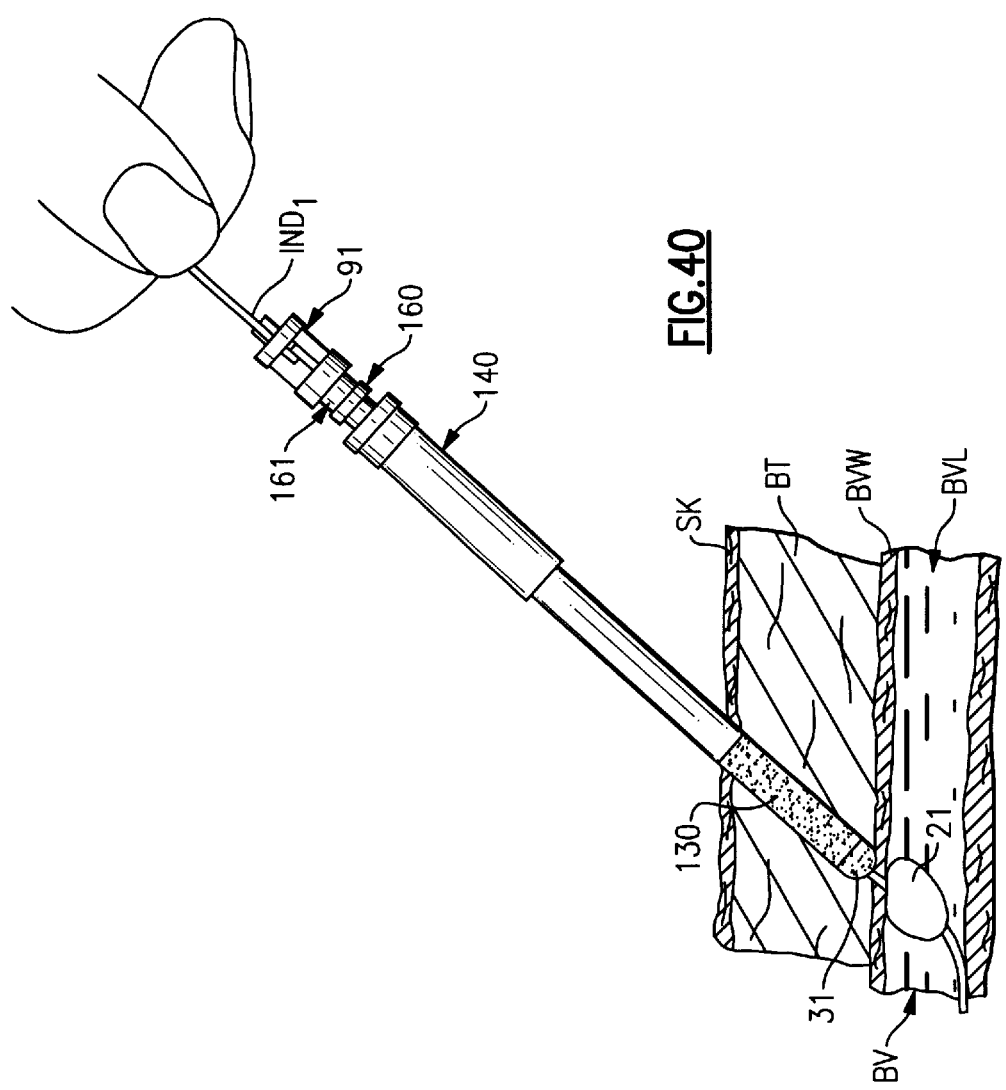
FIG. 40 illustrates the sheath member retracted in the second embodiment of the invention as it is being installed.

The physician then removes the safety pin 195 and the discharge prevention member 191 so that the sheath assembly 140 can be retracted. The sheath member 140 is retracted as seen in FIG. 40 while the delivery assembly 160 serves to hold the sealing material 130 and separator member 31 in place. After this is complete, the physician collapses the balloon 21 and removes it similarly to that of the first embodiment seen in FIG. 29. Finally, the physician removes the guide tube assembly 48 like the first embodiment seen in FIG. 30 to complete the operation.

Third Embodiment of Installation Arrangement:

The third embodiment of the installation arrangement designated 212 is best seen in FIGS. 41–45. The installation arrangement 212 is also designed to place a flowable sealing material 230 into the puncture PP and uses the separator member 31 to separate the flowable sealing material 230 from the blood vessel wall and the end of the puncture opening into the blood vessel lumen BVL. The installation arrangement 212 includes a delivery assembly 260 carrying the sealing material 230 and separator member 31, and a plunger means 261 to hold the material 230 and member 31 in a fixed position while the delivery assembly 260 is moved relative thereto as will become more apparent.

The delivery assembly 260 seen in FIGS. 41 and 42 includes delivery tube 262 with a projecting leading end 264 thereon and with a pair of opposed gripping ears 265 at the opposite end thereof. The delivery tube 262 has an elongate tubular side wall 266 with central axis $A_{20}$. The side wall is stepped intermediate its length so as to form a thinner puncture entering section 268 along the leading portion thereof and a thicker base section along the trailing portion thereof. The puncture entering section 268 has a length greater than the greatest length of puncture PP likely to be encountered so that the base section does not have to enter the puncture. The outside diameter $D_{20}$ of the thinner puncture entering section 268 is as small as possible while still providing sufficient strength to prevent failure of the delivery tube 262 during use. In this particular illustration, the diameter $D_{20}$ is about 0.122 inch. The tube 262 defines a common passage 269 therethrough with diameter $D_{21}$ to receive the plunger means 261 therein as will become more apparent. A funnel shaped separator wall section 270 integral with the side wall 266 and located adjacent the leading end 264 of the tube 262 projects into the passage 269 to divide the passage into a separator holding chamber $HC_S$ at the leading end 264 of the tube 262 and a mixing chamber 271 immediately therebehind. A separator arrangement 272 is provided inside the tube 262 upstream of the mixing chamber 271 to divide the passage 269 into a pair of sealing material holding chambers $RC_{SM}$. The arrangement 272 includes a central tubular section 274 defining a central passage 275 therethrough to slidably receive the guide tube 49 on the guide tube assembly 48 therethrough and a pair of opposed, radially extending partition walls 276 integral with and extending between the central tubular section 275 and the side wall 266. The leading ends of the holding chambers $RC_{SM}$ are closed by a rupturable seal 277 between the arrangement 272 and the side wall 266.

The plunger means 261 corresponds to the means 61 of the first embodiment of the invention except that it is adapted to be received over the separator arrangement 272 to force the sealing material 230 and the separator member 31 out of the delivery tube 262. Both the resilient discharge piston 278 and its central support shaft 279 define a clearance passage 280 therethrough to receive the central tubular section 274 of the arrangement 272 and are slotted at 281 on opposite sides thereof to pass over the partition walls 276. The handle 282 is similar to that of the first embodiment of the plunger means and an abutment 284 is provided to limit the retraction of the delivery tube 262 over the plunger means 261.

The fibrin sealing material 230 is also illustrated as a two component material in the drawings for simplicity without limiting of the intended coverage. The uncured sealing material components $230_A$ and $230_B$ are each loaded in one of the chambers $RC_{SM}$ as best seen in FIG. 45 and the plunger means 261 installed therebehind to capture the components $230_A$ and $230_B$ between the seal 277 and the piston 278. When the delivery tube 262 is retracted over the plunger means 261, the piston 278 causes the seal 277 to rupture, the two components to mix in the mixing chamber 271, and then pass out through the funnel shaped wall section 270 behind the separator member 31. This also causes the mixed fibrin sealing material 230 to force the separator member 31 out of the end 264 of the tube 262. The discharge prevention member 81 used with the first embodiment of the delivery assembly is used with the third embodiment.

Use of Third Embodiment of Installation Arrangement:

The third embodiment 212 of the installation arrangement is also used with the temporary sealing arrangement 11. The steps using the third embodiment 212 correspond to those using the first embodiment 12 as seen in FIGS. 24–30.

What is claimed is:

1. A method of closing a percutaneous puncture made through the body of a patient to gain access to a blood vessel, comprising the steps of:
   a. inserting in the puncture a tube containing a flowable biocompatible adhesive not in contact with a channel so as to form the channel in the puncture from outside of the body to an area proximate to the outside of a blood vessel exterior wall;
   b. removing the tube so as to deposit the flowable biocompatible adhesive in the channel and outside of the blood vessel exterior wall while preventing flow of the adhesive out of the end of the puncture into the blood vessel and preventing the flow of body fluid out of the blood vessel; and,
   c. allowing the biocompatible adhesive to bond the puncture together to close the puncture while substantially preventing the flow of body fluid from the blood vessel from coming into contact with the biocompatible adhesive.

2. A method of closing closing a percutaneous puncture made through the body of a patient to gain access to a blood vessel, comprising the steps of:
   a. temporarily closing that end of the puncture through the body of the patient opening into the blood vessel;
   b. inserting in the puncture a tube containing a flowable biocompatible adhesive not in contact with a channel so as to form the channel in the puncture from outside of the body to i area proximate to the outside of a blood vessel exterior wall;
   c. removing the tube so as to deposit the biocompatible adhesive in the channel and outside of the blood vessel exterior wall while that end of the puncture opening into the blood vessel is temporarily closed so that a portion of the biocompatible adhesive is located adjacent the temporarily closed end of the puncture while preventing the flow of blood such that the adhesive does not contact an appreciable amount of body fluid within the blood vessel;
   d. allowing the biocompatible adhesive to set sufficiently to maintain the puncture substantially closed while the end of the puncture is maintained closed to prevent the biocompatible adhesive from flowing out of the end of the puncture; and,
   e. removing the temporary closure of that end of the puncture opening into the blood vessel through the biocompatible adhesive.

3. The method of claim 2, further comprising:
   a. placing a bioabsorbable separator member in the puncture adjacent the opening of the puncture into the blood vessel between steps a) and b) so that the bioabsorbable separator member prevents the biocompatible adhesive from flowing into the blood vessel while the adhesive bonds to the bioabsorbable separator member as an incident to the bonding of the biocompatible adhesive to close the puncture to retain the bioabsorbable separator member in the puncture.

4. The method of claim 2, wherein step a) includes the substeps of:
   a) inserting an expandable member attached to a control member into the blood vessel through the puncture while the expandable member is in a collapsed condition smaller than the puncture opening so that the control member extends out of the puncture exteriorly of the patient,
   b) expanding the expandable member to an expanded condition larger than the puncture opening, and
   c) pulling the expanded expandable member back against the end of the puncture opening into the body cavity using the control member to substantially close the end of the puncture; and, and wherein step d) further comprises the substeps of;
   d) collapsing the expandable member back to the collapsed condition smaller than the puncture opening; and e) retracting the collapsed expandable member and control member through the adhesive while leaving the adhesive in position to maintain the puncture sealed.

5. The method of claim 2, wherein the biocompatible adhesive is activated by ultraviolet light in situ and further including the step of exposing the biocompatible adhesive to ultraviolet light prior to step b).

6. The method of claim 2, further including the step of positioning the biocompatible adhesive on a central guide tube defining a central passage therethrough for use in installing said biocompatible adhesive.

* * * * *